United States Patent
Golden et al.

(10) Patent No.: US 12,023,002 B2
(45) Date of Patent: *Jul. 2, 2024

(54) ATTACHMENT CLAMP

(71) Applicant: Boston Scientific Scimed, Inc., Maple Grove, MN (US)

(72) Inventors: John B. Golden, Norton, MA (US); John O. McWeeney, Brighton, MA (US); Christopher A. Benning, Hopkinton, MA (US); Robert Castoldi, Marlborough, MA (US); John F. Howard, Salem, MA (US); Brian Intoccia, Denver, CO (US); Gary Kappel, Acton, MA (US); William L. Churchill, Bolton, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/189,300

(22) Filed: Mar. 24, 2023

(65) Prior Publication Data

US 2023/0225589 A1 Jul. 20, 2023

Related U.S. Application Data

(63) Continuation of application No. 18/057,485, filed on Nov. 21, 2022, now Pat. No. 11,737,654, which is a
(Continued)

(51) Int. Cl.
*A61B 1/00* (2006.01)
*A61B 1/018* (2006.01)
(Continued)

(52) U.S. Cl.
CPC ........ *A61B 1/00128* (2013.01); *A61B 1/0014* (2013.01); *A61B 1/018* (2013.01);
(Continued)

(58) Field of Classification Search
CPC ... A61B 1/00128; A61B 1/0014; A61B 1/018; F16B 2/08
(Continued)

(56) References Cited

U.S. PATENT DOCUMENTS 3,706,437 A 12/1972 Eberhardt
4,493,468 A 1/1985 Roach
(Continued)

FOREIGN PATENT DOCUMENTS

| WO | 2006033671 A2 | 3/2006 |
| WO | 2006063497 A1 | 6/2006 |
| WO | 2007109209 A2 | 9/2007 |

OTHER PUBLICATIONS

International Search Report and Written Opinion of the International Search Authority dated Jun. 19, 2008, issued in corresponding International Application No. PCT/US2008/053313, file Feb. 7, 2008.

*Primary Examiner* — Todd M Epps
(74) *Attorney, Agent, or Firm* — Bookoff McAndrews, PLLC

(57) ABSTRACT

Various apparatuses to attach a first medical device to a second medical device are described that allow the physician to grasp only a single device while the other device remains securely attached to the one being grasped. The apparatuses, once they are attached to the first medical device, are designed to be easily and quickly attached and detached to a second medical device, normally only requiring the use of one hand. Furthermore, the apparatuses oftentimes include a base that can easily couple and decouple from the portion that is attached to the second medical device so that if the need arises to separately use the second medical device, it can be decoupled from the first medical device without completely removing the apparatus from the second medical device.

21 Claims, 23 Drawing Sheets

Related U.S. Application Data continuation of application No. 17/855,881, filed on Jul. 1, 2022, now Pat. No. 11,622,670, which is a continuation of application No. 17/106,817, filed on Nov. 30, 2020, now Pat. No. 11,406,247, which is a continuation of application No. 16/695,679, filed on Nov. 26, 2019, now Pat. No. 10,881,274, which is a continuation of application No. 16/233,551, filed on Dec. 27, 2018, now Pat. No. 10,524,638, which is a continuation of application No. 15/837,460, filed on Dec. 11, 2017, now Pat. No. 10,201,264, which is a continuation of application No. 15/398,490, filed on Jan. 4, 2017, now Pat. No. 9,867,522, which is a continuation of application No. 14/517,290, filed on Oct. 17, 2014, now Pat. No. 9,565,992, which is a continuation of application No. 13/714,110, filed on Dec. 13, 2012, now Pat. No. 8,894,028, which is a continuation of application No. 12/526,469, filed as application No. PCT/US2008/053313 on Feb. 7, 2008, now Pat. No. 8,353,493.

(60) Provisional application No. 60/888,713, filed on Feb. 7, 2007.

(51) Int. Cl.
    *F16B 2/08* (2006.01)
    *F16B 2/10* (2006.01)
    *F16B 2/12* (2006.01)
    *F16B 2/18* (2006.01)
    *F16B 2/22* (2006.01)

(52) U.S. Cl.
    CPC ............... *F16B 2/08* (2013.01); *F16B 2/10* (2013.01); *F16B 2/12* (2013.01); *F16B 2/185* (2013.01); *F16B 2/22* (2013.01); *Y10T 24/1482* (2015.01); *Y10T 24/44017* (2015.01)

(58) Field of Classification Search
    USPC ........................................... 248/316.5
    See application file for complete search history.

(56) References Cited

U.S. PATENT DOCUMENTS

| | | |
|---|---|---|
| 4,875,647 A | 10/1989 | Takagi et al. |
| 5,131,613 A | 7/1992 | Kamiya et al. |
| 5,755,225 A | 5/1998 | Hutson |
| 6,196,033 B1 | 3/2001 | Dowdle |
| 6,364,257 B1 | 4/2002 | Holder |
| 6,408,850 B1 | 6/2002 | Sudge |
| 6,684,667 B2 | 2/2004 | Young |
| 6,807,714 B2 | 10/2004 | O'Young et al. |
| 6,976,980 B2 | 12/2005 | Brenner et al. |
| 7,131,168 B2 | 11/2006 | Pangallo |
| 7,284,302 B2 | 10/2007 | Lares |
| 7,753,321 B2 | 7/2010 | Geiger |
| 7,762,503 B2 | 7/2010 | Franks |
| 7,775,484 B2 | 8/2010 | Gunzburger |
| 7,866,617 B2 | 1/2011 | Kleitsch et al. |
| 7,900,324 B2 | 3/2011 | Ginocchio |
| 7,913,959 B2 | 3/2011 | White et al. |
| 7,997,542 B2 | 8/2011 | Morello |
| 8,353,493 B2 * | 1/2013 | Golden .................. F16B 2/185 |
| | | 248/230.7 |
| 8,894,028 B2 * | 11/2014 | Golden .................. F16B 2/22 |
| | | 248/231.71 |
| 9,565,992 B2 * | 2/2017 | Golden .................. F16B 2/10 |
| 9,867,522 B2 * | 1/2018 | Golden .................. F16B 2/185 |
| 10,201,264 B2 * | 2/2019 | Golden .................. F16B 2/08 |
| 10,524,638 B2 * | 1/2020 | Golden .................. F16B 2/08 |
| 10,881,274 B2 * | 1/2021 | Golden .................. A61B 1/018 |
| 11,406,247 B2 * | 8/2022 | Golden .................. F16B 2/10 |
| 11,737,654 B2 * | 8/2023 | Golden .................. F16B 2/22 |
| | | 248/316.5 |
| 2004/0011928 A1 | 1/2004 | Helot et al. |
| 2005/0272975 A1 | 12/2005 | McWeeney et al. |
| 2006/0009680 A1 | 1/2006 | Dhindsa |
| 2006/0135846 A1 | 6/2006 | Hunt |
| 2006/0258908 A1 | 11/2006 | Stefanchik et al. |

* cited by examiner

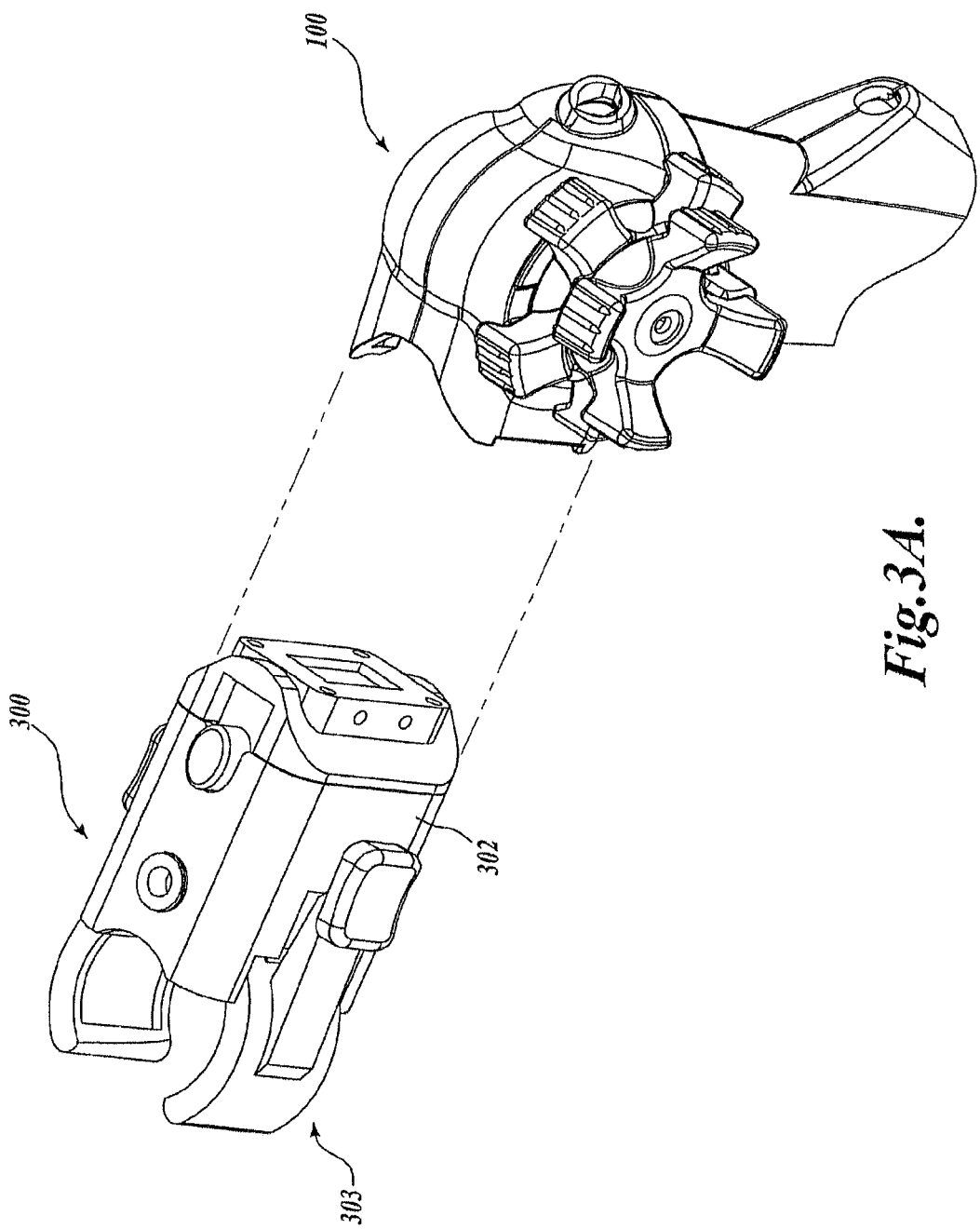

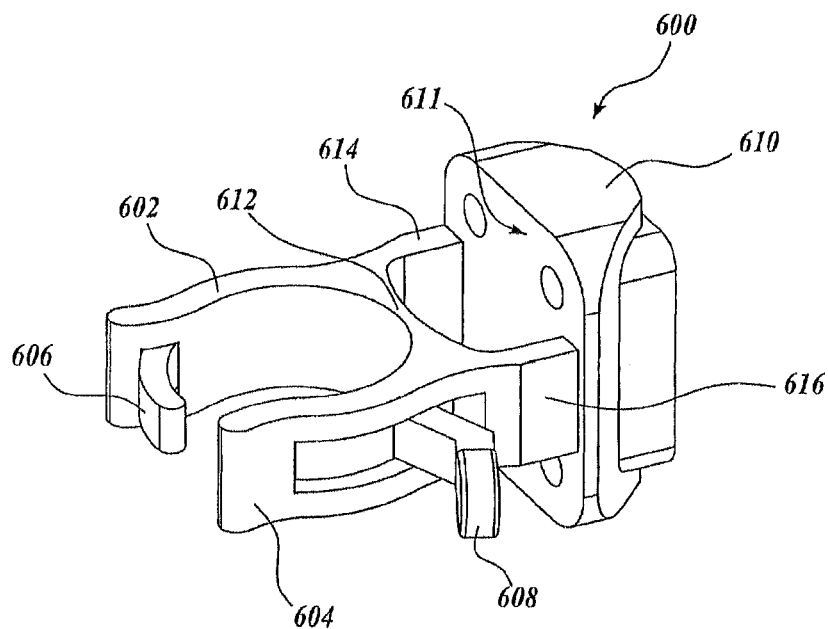
*Fig.6A.*
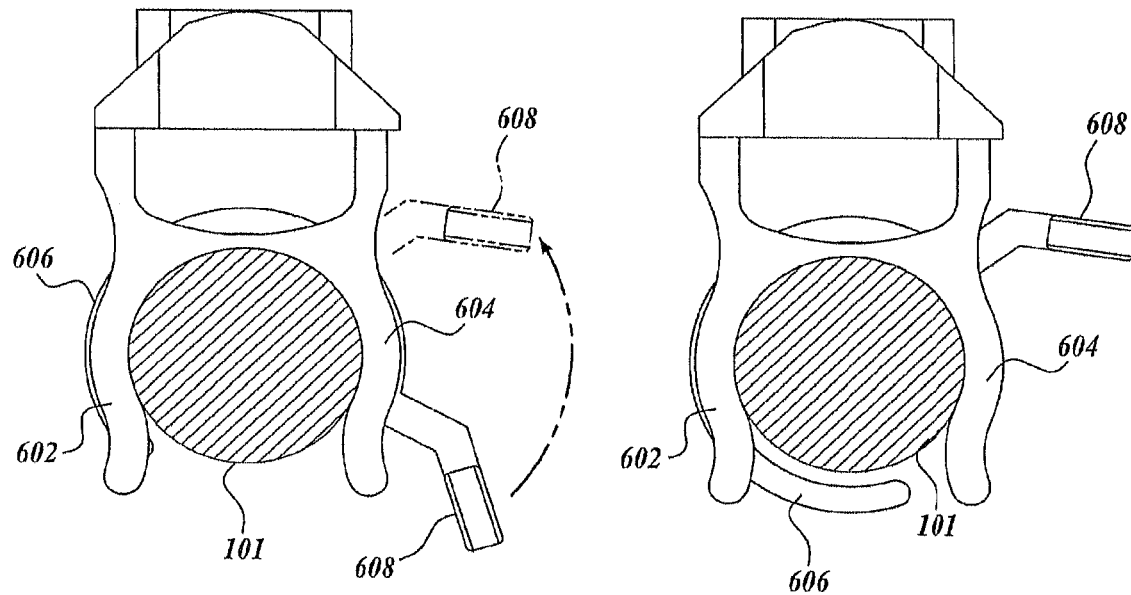
*Fig.6B.* *Fig.6C.*

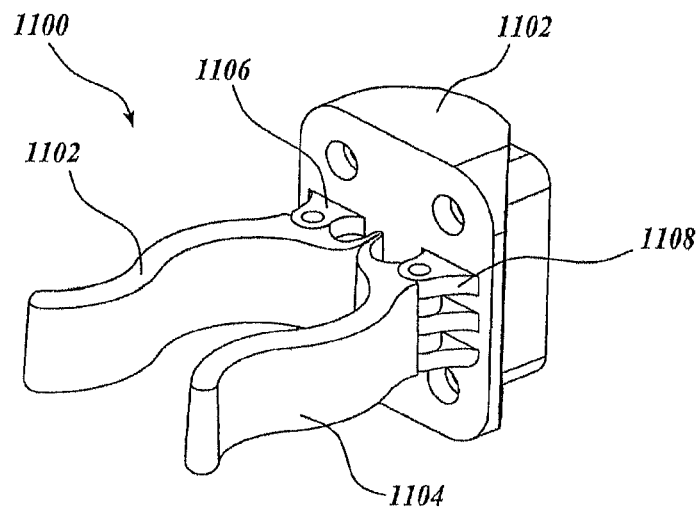
Fig.11A.
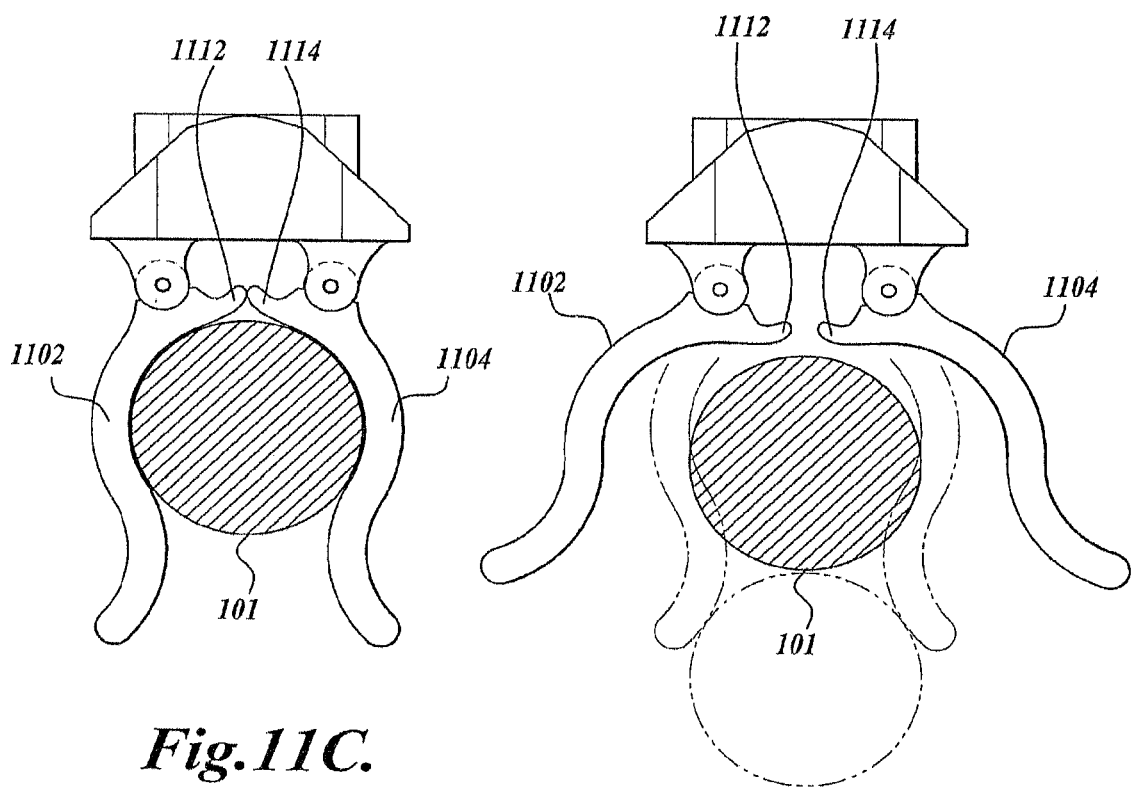
Fig.11C.
Fig.11B.

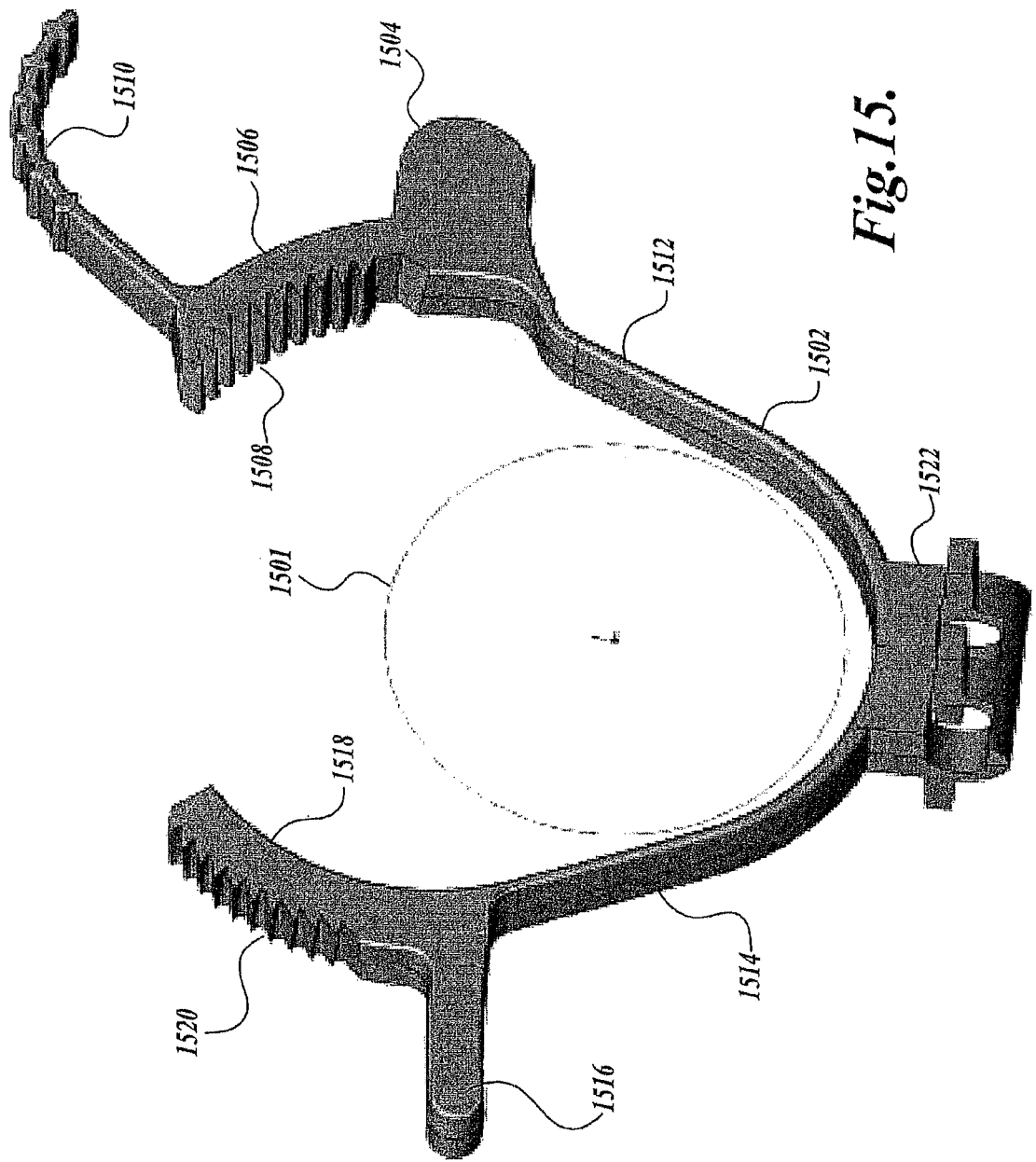

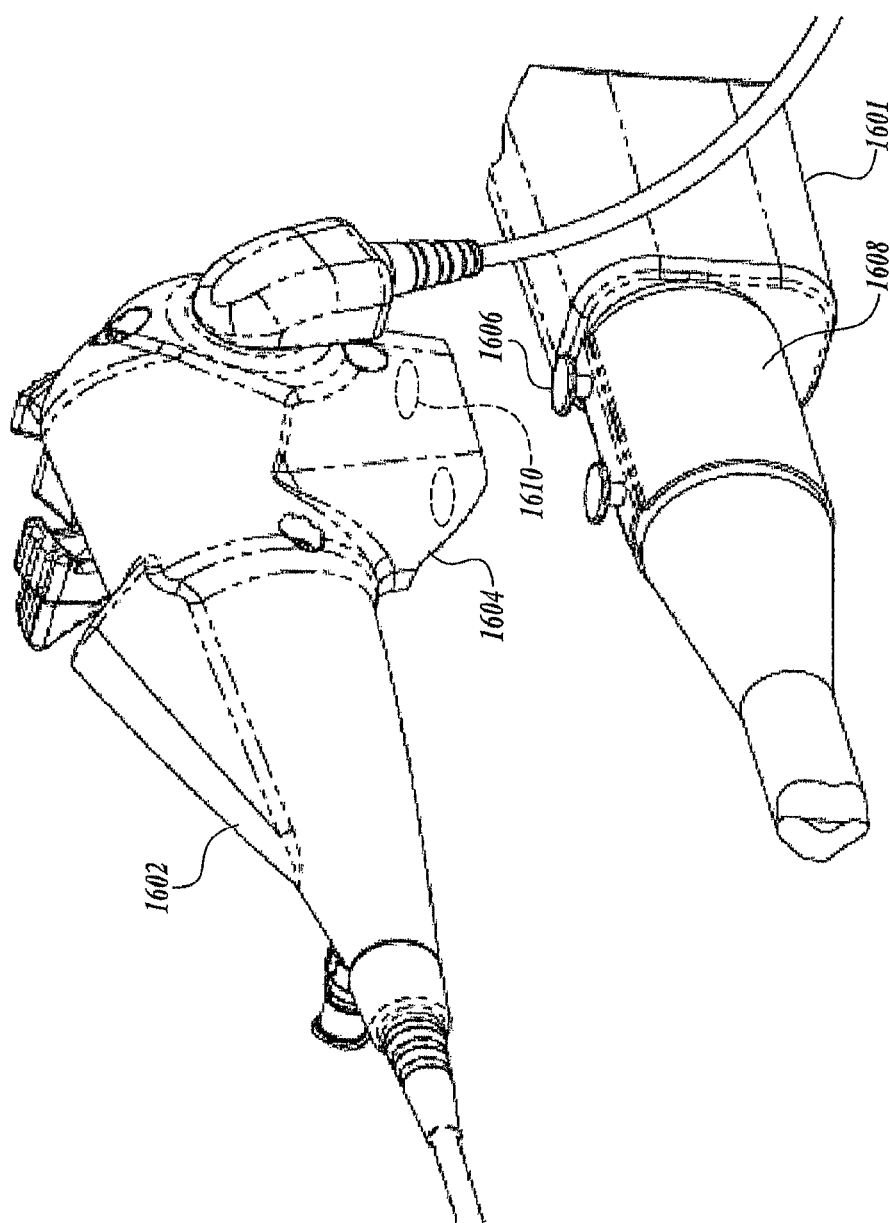

ATTACHMENT CLAMP

CROSS-REFERENCE TO RELATED APPLICATION

This application is a continuation of U.S. patent application Ser. No. 18/057,485, filed Nov. 21, 2022, which is a continuation of U.S. patent application Ser. No. 17/855,881, filed Jul. 1, 2022, which is a continuation of U.S. patent application Ser. No. 17/106,817, filed Nov. 30, 2020, now U.S. Pat. No. 11,406,247, issued Aug. 9, 2022, which is a continuation of U.S. patent application Ser. No. 16/695,679, filed Nov. 26, 2019, now U.S. Pat. No. 10,881,274, issued Jan. 5, 2021, which is a continuation of U.S. patent application Ser. No. 16/233,551, filed Dec. 27, 2018, now U.S. Pat. No. 10,524,638, issued Jan. 7, 2020, which is a continuation of U.S. patent application Ser. No. 15/837,460, filed Dec. 11, 2017, now U.S. Pat. No. 10,201,264, issued Feb. 12, 2019, which is a continuation of U.S. patent application Ser. No. 15/398,490, filed Jan. 4, 2017, now U.S. Pat. No. 9,867,522, issued Jan. 16, 2018, which is a continuation of U.S. patent application Ser. No. 14/517,290, filed Oct. 17, 2014, now U.S. Pat. No. 9,565,992, issued Feb. 14, 2017, which is a continuation of U.S. patent application Ser. No. 13/714,110, filed Dec. 13, 2012, now U.S. Pat. No. 8,894,028, issued Nov. 25, 2014, which is a continuation of U.S. application Ser. No. 12/526,469, filed Jan. 18, 2011, now U.S. Pat. No. 8,353,493, issued Jan. 15, 2013, which is the National Stage entry under 35 U.S.C. § 371 of PCT/US2008/053313, filed Feb. 7, 2008, which claims the benefit of U.S. Provisional Application No. 60/888,713, filed Feb. 7, 2007, all of which are incorporated herein by reference in their entireties.

BACKGROUND

More than one medical device is often required to be used together during the same medical procedure. For example, in the performance of minimally-invasive types of procedures using an endoscope, a second medical device is sometimes inserted through the working channel of the endoscope. Either the endoscope or the second medical device can provide illumination and imaging capability while the other may perform a distinct or specialized function. Having to hold two instruments is burdensome for the physician.

SUMMARY

Various apparatuses to attach a first medical device to a second medical device are described that allow the physician to grasp only a single device while the other device remains securely attached to the one being grasped. Embodiments of the apparatus may include one or more of the following devices or a type of holding portion including clamps, jaws, pincers, latches, toggle joints, hooks, straps, fasteners, buckles and the like that are modified for use in holding the second medical device securely onto the first medical device. Additionally or alternatively, any of the devices or holding portions can have surfaces covered by means to enhance the gripping strength between the holding portion and the medical device. For example, the clamps, jaws, pincers, latches, joints, hooks, straps, fasteners, and buckles can have surfaces that enhance gripping including a soft material, a sticky or tacky material such as a releasable adhesive, magnets, keyed features (i.e., components that fit within other slots or notches), VELCRO® enhancements at any surface, surface roughening, and/or additional material wrapped around the catheter. The apparatuses, once they are attached to the first medical device, are designed to be easily and quickly attached and detached to a second medical device, normally only requiring the use of one hand. Furthermore, the apparatuses oftentimes include a base attached to the first medical device that can easily couple and decouple from the portion that is attached to the second medical device so that if the second medical device needs to be operated by a different user, the second medical device can be decoupled from the first medical device without completely removing the apparatus from the second medical device.

While the apparatuses are described as being used with a first medical device and a second medical device, the apparatuses are thereby not limited solely to use in a medical setting. The description with reference to medical devices is done solely for the purpose of illustrating a representative use. The apparatuses herein disclosed may be used, for example, to hold any two tools to each other where the job or task requires that two tools be used. Such tools may include tools of a mechanic, plumber, electrician, or any other trade.

This summary is provided to introduce a selection of concepts in a simplified form, concepts that are further described below in the Detailed Description. This summary is not intended to identify key features of the claimed subject matter nor is it intended to be used as an aid in determining the scope of the claimed subject matter.

DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein;

FIGS. 3A-3B are diagrammatical illustrations of an apparatus to attach a first medical device to a second medical device in accordance with another embodiment of the present invention;

FIGS. 6A-6C are diagrammatical illustrations of an apparatus to attach a first medical device to a second medical device in accordance with another embodiment of the present invention;

FIGS. 11A-11C are diagrammatical illustrations of an apparatus to attach a first medical device to a second medical device in accordance with another embodiment of the present invention;

FIG. 15 is a diagrammatical illustration of an apparatus to attach a first medical device to a second medical device in accordance with another embodiment of the present invention; and FIG. 16 is a diagrammatical illustration of an apparatus to attach a first medical device to a second medical device in accordance with another embodiment of the present invention.

DETAILED DESCRIPTION

Figure 1A:
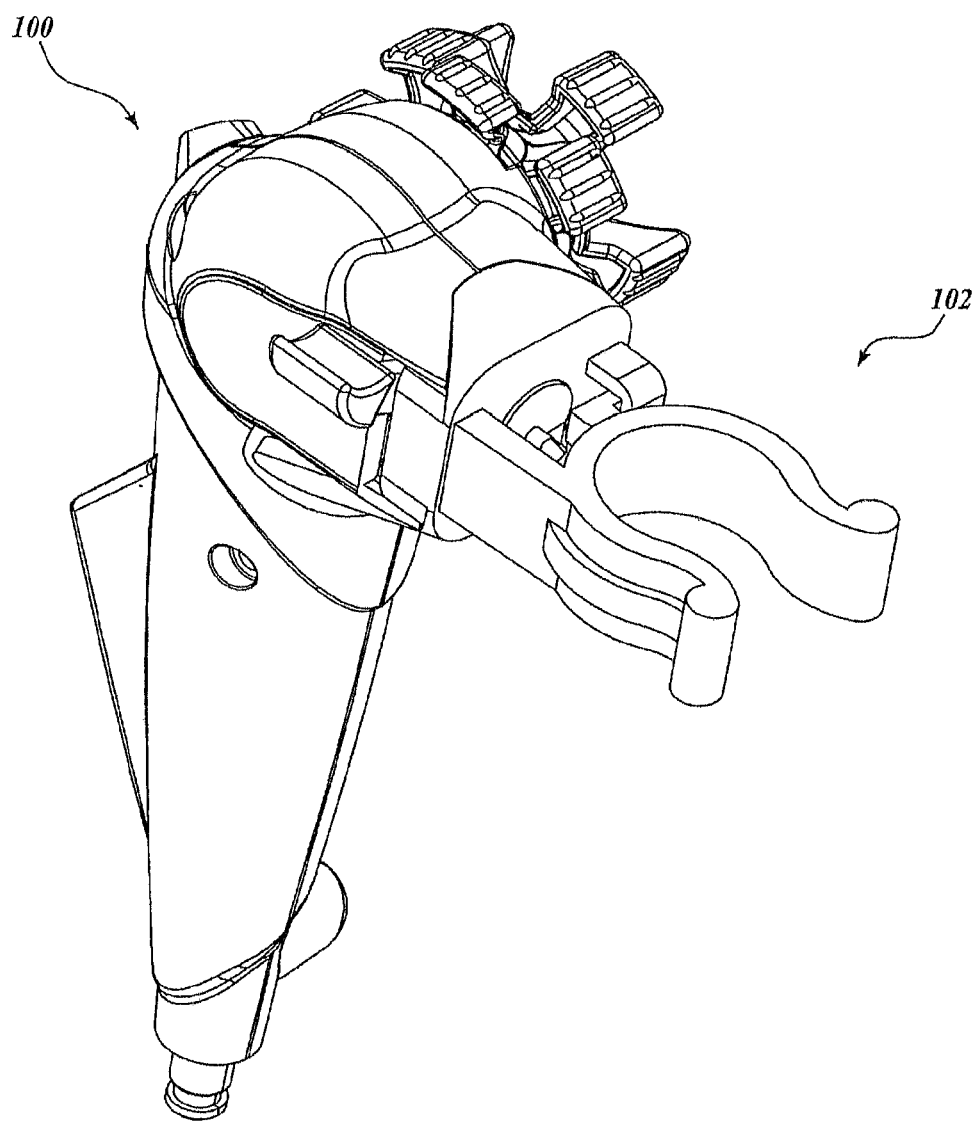
FIGS. 1A-1E are diagrammatical illustrations of an apparatus to attach a first medical device to a second medical device in accordance with one embodiment of the present invention.

Referring to FIG. 1A, a medical device 100 may include an apparatus 102 for attaching the first medical device to a second medical device (not shown). Medical device 100 and the second medical device that is not shown may be an endoscope, a catheter, a minimally invasive device, and the like. Medical devices preferably may have a circular cross-sectional configuration at least along some portion of their length.

Figure 1B:
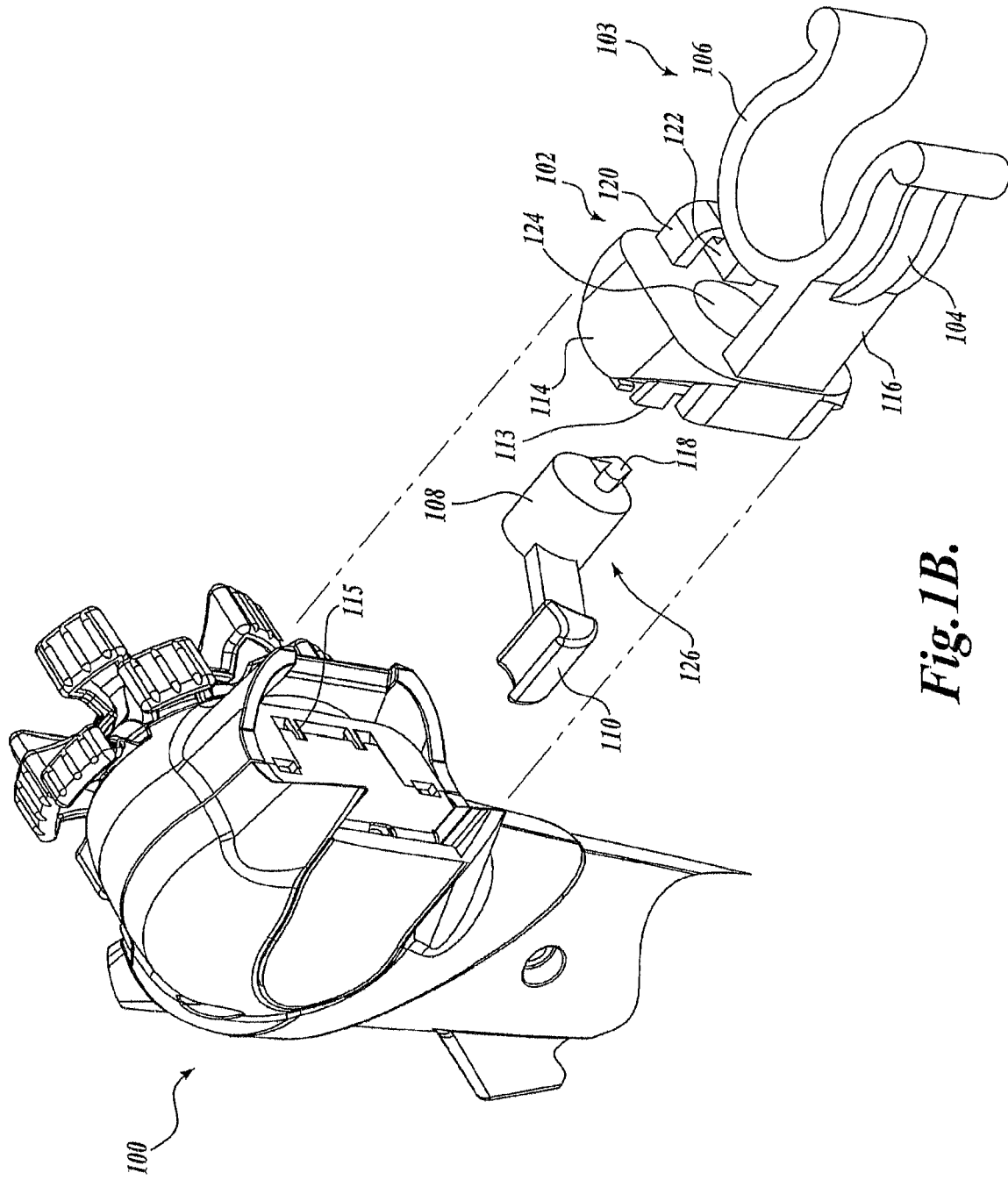

Referring to FIG. 1B, the apparatus 102 may include a clamp 103 portion and a base 114 portion that attach to the medical device 100, The clamp base 114 may attach to the medical device 100 by any sort of mechanical or adhesive means such as fasteners, pins, etc. For example, in one embodiment, the clamp base 114 may include tabs 113 that engage in corresponding slots 115 on the medical device 100. In one embodiment, the clamp base 114 may include an outwardly extending beam 116 to which the clamp 103 is attached, Beam 116 projects perpendicular to the front surface of the base 114. Beam 116 supports the clamp 103, which may be constructed from a first jaw 104 and a second jaw 106. "Jaws," as used herein, may be any holding portion or portions that have opposed mating surfaces between which an instrument or device is held. In one embodiment, the jaws may have an arcuate shape such that when placed in a position opposed to one another, the jaws define an open center holding area and have free ends that flare radially outward, creating a guide for leading the second medical device to the center holding area. The jaws 104, 106 may be made from a semi-rigid material that can deform by allowing the jaws to separate at the free ends to allow the second medical device to enter the holding area. The beam 116 may be positioned on one side of the base 114 and may be connected to one side of the clamp 103. In other embodiments, a first jaw and a second jaw may be pivoted to swing in the center and biased closed with a spring such as a coil spring, leaf spring, or other resilient material.

As best seen in FIG. 1B, an L-shaped hook 122 extends from the back of the jaw 106 towards the base 114 on the side opposite to the beam 116. The L-shaped hook 122 has a tab projecting parallel to the front surface of the base 114 that can move into and out of a catch 120 secured to the clamp base 114. In one embodiment, the catch 122 is an arcuate member having a pair of legs secured to the base 114 and an opening therein into which the tab of the hook 122 can fit. In a static condition, the tab of the hook 122 fits within the opening of the catch 122 so that the tab is at least partially covered by the catch 120.

The tab of the hook 122 is movable to a second position where the tab is disengaged from the catch 120, The tab of the hook 122 moves from beneath the catch 120 when the jaw 106 is deflected. For example, when a second medical device is forced through the ends of the jaws 104 and 106, the width at the entrance increases, which causes the jaw 106 to be deflected outward and the tab of the hook 122 to Move out from under the catch 120, When the second medical device passes the narrower entrance between jaws 104 and 106 and into the holding area of the clamp, the jaw 106 returns to its undeflected position and the tab of the hook 122 returns to lying underneath or being positioned within the catch 120.

In the embodiment shown, the clamp 103 also includes a locking mechanism 126 that may comprise a barrel 108, a lever 110, and a pawl 118. The pawl 118 is positioned at the distal end of the barrel 108 and on the flat surface that is perpendicular to the long axis of the barrel 108, The lever 110 may extend outwardly from the opposite end of the barrel 108 so that movement of the lever 110 causes the barrel 108 to rotate about its longitudinal axis. The locking mechanism 126 is rotatably positioned within a hole 124 in the base 114 so that the pawl 118 protrudes past the surface of the base 114 and is able to reach to the hook 122. The pawl 118 may include a ridge and a ramp placed orthogonal to the ridge. The base 114 retains the barrel 108 within the hole 124 when the base 114 is connected to the medical device 100. In another embodiment, the lever 110 may be replaced by a dial that may be rotated to adjust the tension with which the device is held between the jaws.

Figure 1C:
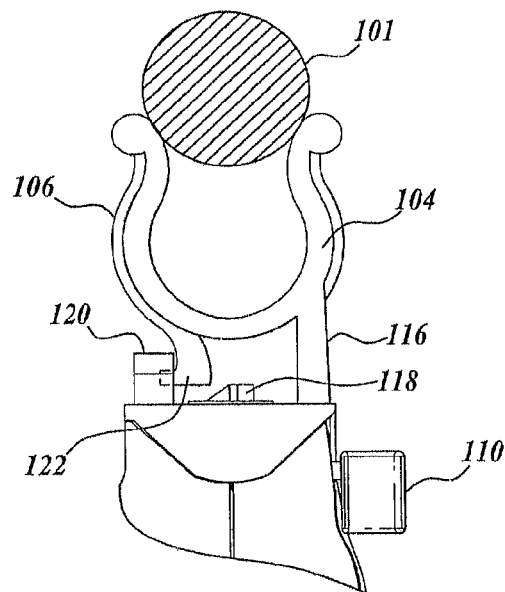
Figure 1D:
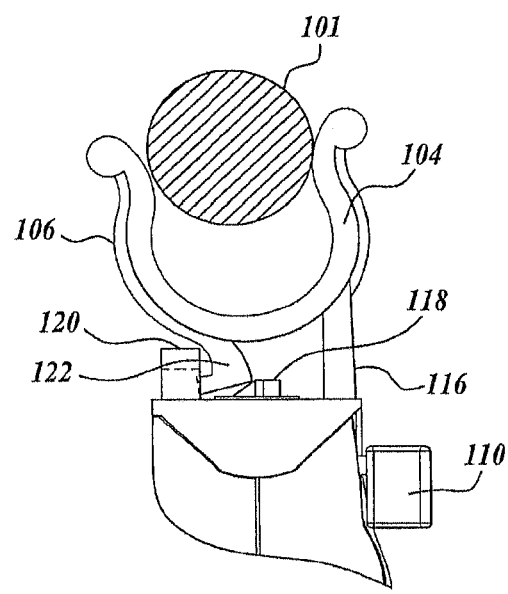
Figure 1E:
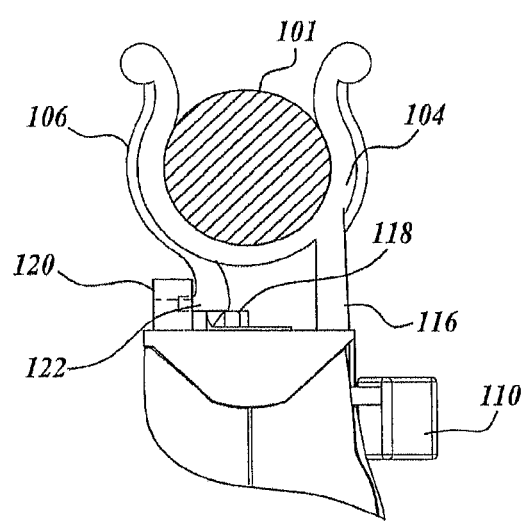

Referring to FIGS. 1C-1E, the second medical device 101 is pressed against the ends of the jaws 104 and 106 that cause the jaws to flex. In FIG. 1C, the pawl 118 is positioned so as not to interfere with the hook 122 movement as the jaw 106 flexes. In FIG. 1D, as the width at the opening increases, the hook 122 moves away from under the catch 120 as the jaws 104 and 106 flex outward. In FIG. 1E, the second medical device 101 is fully captured by jaws 104 and 106, and the hook 122 returns to within catch 120. The lever 110 can be pressed to rotate the barrel 108 and cause the pawl 118 to engage the hook 122. The pawl 118 first engages the back of the hook 122 with the ramp to apply pressure that presses the hook 122 upward so that the pawl 118 will push the hook 122 against the catch 120. Continued rotation of the barrel eventually pushes the hook up and above the top surface of the pawl 118 onto the ridge. This action will pinch the second medical device 101 tighter within clamp 102. With the ramp touching the hook 122 and keeping the hook 122 in the catch 120, the jaws 104 and 106 are prevented from flexing, thus, retaining the second medical device 101 within the clamp 103.

The inside surfaces of the jaws 104 and 106 may be covered by means to enhance the gripping strength between the jaws and the medical device. For example, the surfaces can have means to enhance gripping, including a soft, pliable material, a sticky or tacky material such as a releasable adhesive, magnets, keyed features (i.e., components that fit within other slots or notches), VELCRO®, surface roughening, and/or additional material wrapped around the catheter.

Figure 2A:
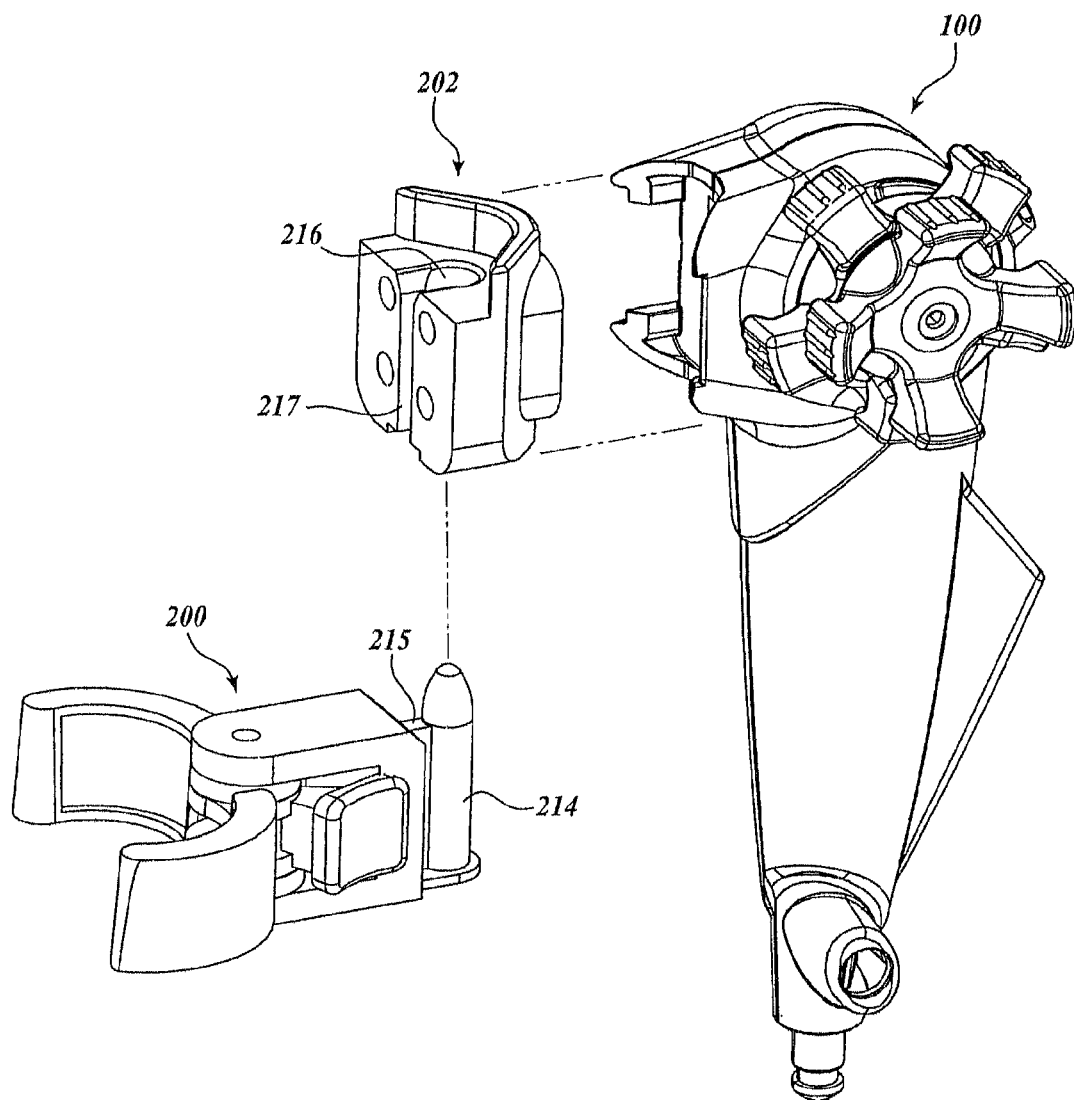
FIGS. 2A-2B are diagrammatical illustrations of an apparatus to attach a first medical device to a second medical device in accordance with another embodiment of the present invention.
Figure 2B:
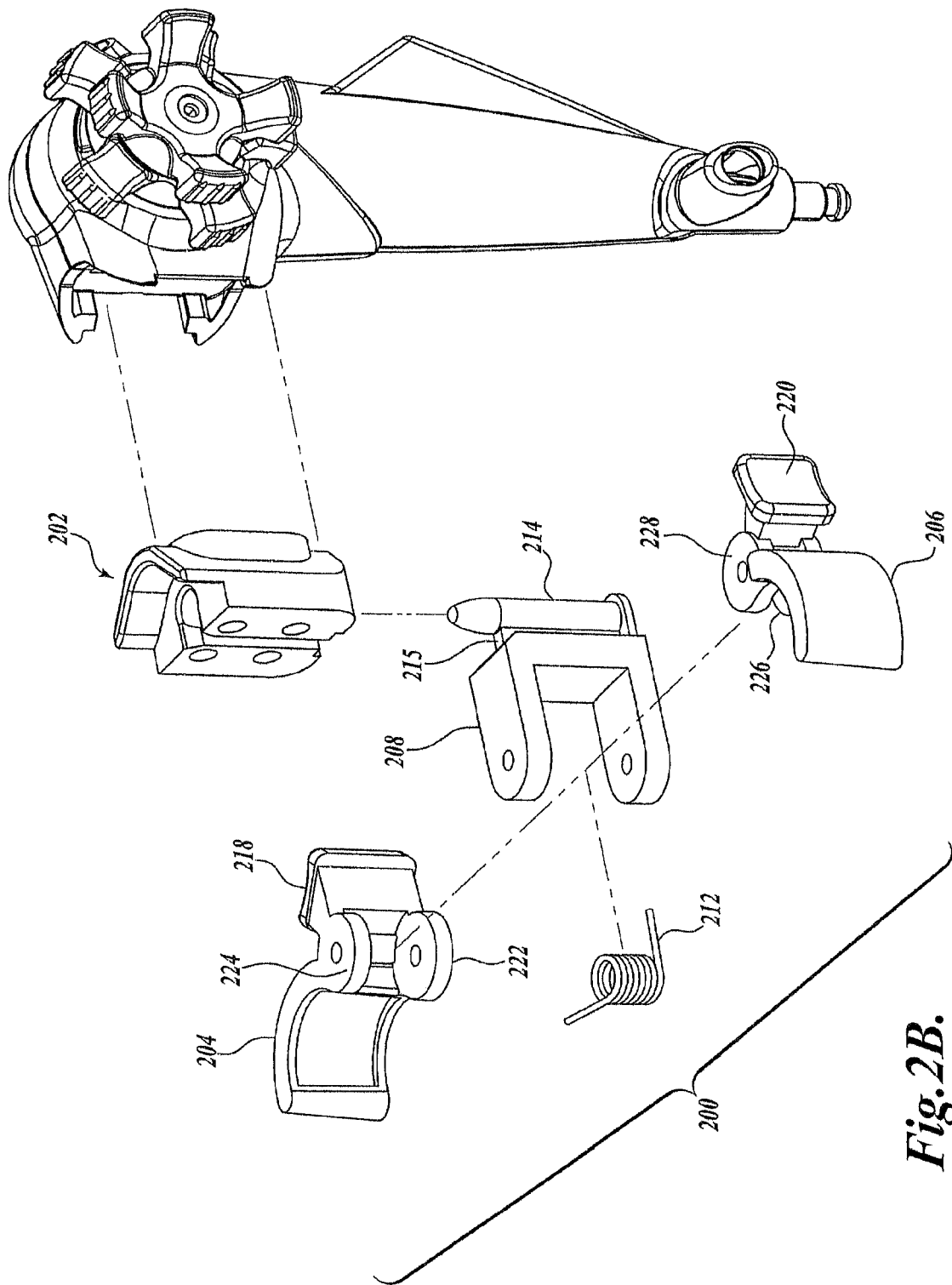

Referring to FIGS. 2A-2B, another embodiment of an apparatus for attaching a first medical device 100 to a second medical device is illustrated. The apparatus may include a base component 202 and a detachable pincer component 200. The medical device 100 may have structure that attaches to the base component 202. The base 202 may be attached to the medical device 100 via any mechanical fastener or may be integrated with other components of the medical device 100. In the illustrated embodiment, the base component 202 may be attached to the medical device 100 via screws that are threaded from one side of the base 202. The base 202 includes an aperture 216 that extends vertically from top to bottom and faces away from the medical device 100, The aperture 216 extends into a slot 217 that also extends vertically on the front surface of the base 202. The pincer component 200 includes a post 214 that slides into the aperture 216 of the base 202 from below. The pincer component 200 includes a web 215 that connects the post 214 to the pincer component 200, The web 215 slides within the slot 217, while the post 214 slides into the aperture 216 to allow the pincer component 200 to be easily detached from the first medical device 100. The apparatus, once it is attached to the first medical device 100, is designed to be easily and quickly attached and detached to a second medical device, normally only requiring the use of one hand. Furthermore, the base 202 and post 214 allows the second medical device to be easily coupled and decoupled from the first medical device 100 if the need arises for the second medical device to be operated by a different user without having to disengage the second medical device from the jaws 204 and 206, This may be accomplished by simply inserting the post 214 into the base 202 and reversing the process to remove the second medical device.

Referring to FIG. 2B, the pincer 200 is shown in an exploded illustration to more clearly describe the components. The pincer 200 includes a hinge 208, The hinge 208 has a first and a second ear disposed parallel to one another and joined to each other by an upstanding wall so that the first and second ears are spaced vertically from each other, creating a gap. The post 214 may be attached to the rear of the upstanding wall via the web 215. The first and second ears have apertures in alignment with each other to allow a pivoting pin (not shown) to be inserted there through from the top ear to the bottom ear. The pincer 200 may include a first jaw 204 and a second jaw 206. Each jaw has an arcuate portion defining half of the pincer 200 and a lever handle joined to the jaw via a fulcrum structure. The fulcrum is therefore interposed between the jaw and the lever handle. Jaw 204 has lever handle 218 joined to the fulcrum comprising lower ear 222 and upper ear 224. Ears 222 and 224 have apertures similar in size to the apertures in the ears of hinge 208. Jaw 206 has lever handle 220 joined to the fulcrum comprising lower ear 226 and upper ear 228. Ears 226 and 228 have apertures similar in size to the apertures in the ears of hinge 208. Ears 222 and 224 of jaw 204 are spaced wide enough apart from each other to accept ears 226 and 228 of jaw 206, which are spaced closer to each other. The ears 226 and 228 provide a gap vertically between them. The pincer 200 is constructed by joining jaws 204 and 206 together with the hinge 208 and positioning the coil spring 212 coaxially with the apertures on the hinge 208, Alternate embodiments may eliminate the coil spring 212 and have flat leaf springs or resilient, but flexible, materials to serve as the biasing device biasing the jaws 204 and 206 together. The spring 212 can fit between lower ear 226 and upper ear 228 of jaw 206. The retaining pin (not shown) may pass through the apertures in the hinge 208 and the apertures 222, 224, 226 and 228 of jaws 204 and 206, The spring 212 may have straight runs at both ends so that the ends can be placed to press against the inside of the lever handles 218 and 220 so that the spring 212 biases the lever handles 218 and 220 outward. Therefore, due to the action of the fulcrums, the jaws 204 and 206 are biased by spring 212 inwardly to close, By pressing on the lever handles 218 and 220, the jaws 204 and 206 are forced open against the action of the spring 212, thus allowing the pincer 200 to be attached to a second medical device.

In other embodiments, the first and second jaws can be joined to each other via a flexible, but resilient hinge material to eliminate the need for a spring and pivoting pin. Such embodiments may resemble the jaw structure illustrated in FIG. 1A, The inside surfaces of the jaws 204 and 206 may be covered by means to enhance the gripping strength between the jaws and the medical device. For example, the surfaces can have means to enhance gripping, including a soft, pliable material, a sticky or tacky material such as a releasable adhesive, magnets, keyed features components that fit within other slots or notches), VELCRO®, surface roughening, and/or additional material wrapped around the catheter.

Figure 3B:
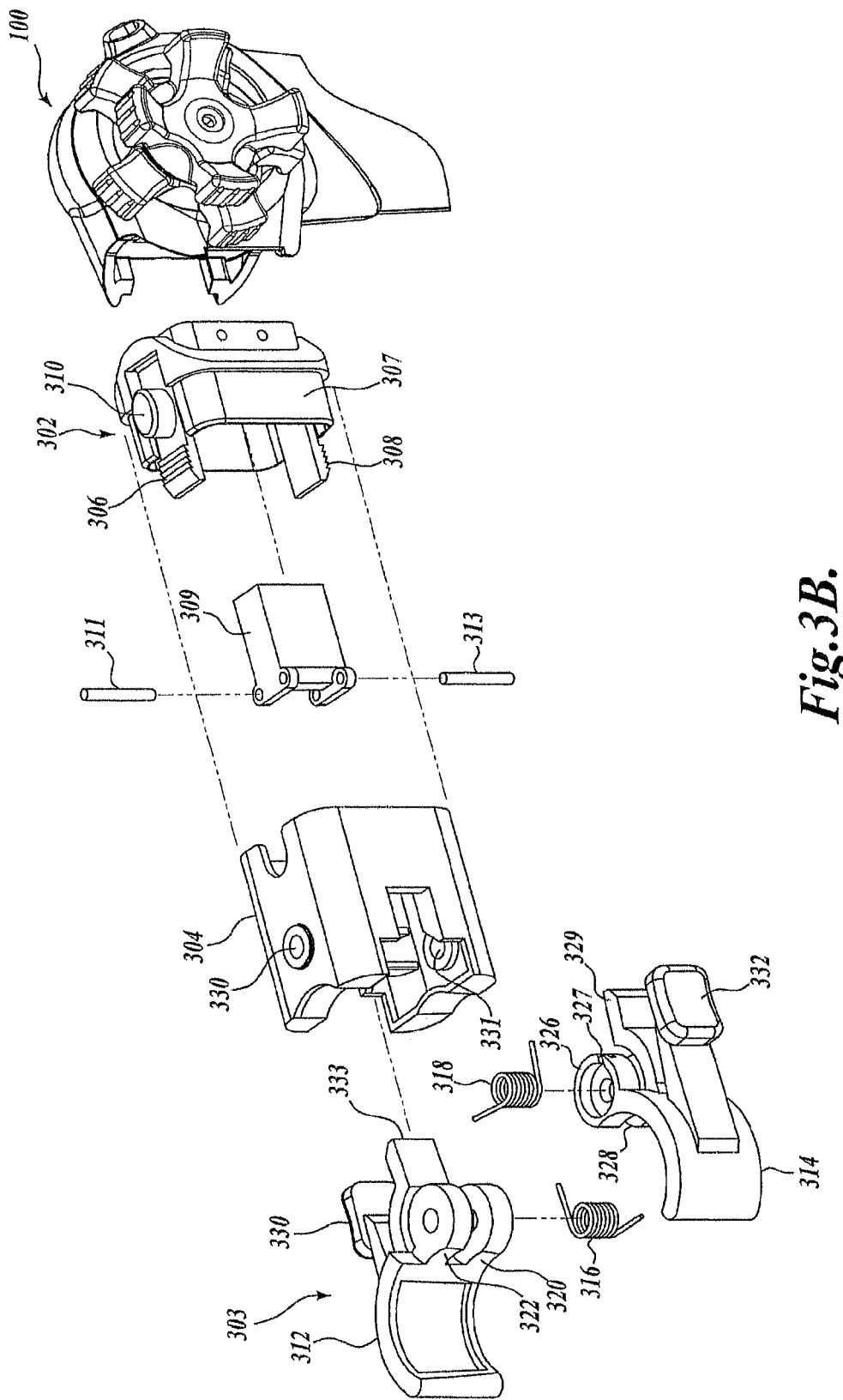

Referring to FIGS. 3A and 3B, an alternate embodiment of an apparatus for attaching a first medical device to a second medical device is illustrated. The apparatus 300 has a spring loaded pincer. The apparatus 300 may include a rack type joint 302 to enable the detachment of the pincer 303 from the medical device 100. The rack type joint 302 may be a box-like structure having two vertical walls and two horizontal walls and a stout rear wall that can be attached to the medical device 100 via mechanical fasteners. The medical device 100, in turn, may have structure to mate with the rack type joint 302 on one side thereof. At the opposite side from the medical device 100, the rack type joint 302 may include means on the top and bottom horizontal walls for detaching the pincer 303 that may include a first tab 306 and a second tab 308 that are flexible to permit deflection in a downward (or upward) motion while hinged at the rear to cause disengagement. The tabs 306 and 308 may have ends with serrations pointing, respectively, up and down, and a button placed at about the middle of the tab. The button may be used as the location to depress the tab.

An intermediate housing 304 that supports the pincer 303 is constructed so as to join to the rack type joint 302. The housing 304 may also be a box-like structure that fits partially over the two vertical and horizontal walls of the rack-type joint. The housing 304 is inserted into the rack-type joint until the walls of the housing 304 hit up against a lip surrounding the rack-type joint. The ends of the tabs 306 and 308 having serrations, therefore, are inserted immediately next to the interior surface of the housing 304 at the top and bottom. The housing 304 has internal mating serrations that engage the serrations of tabs 306 and 308. The button 310 and the second button that is opposite and connected to tab 308, which is not shown, are used to depress tabs 306 and 308 inwardly so as to disengage the housing 304 from the rack-type joint 302, The apparatus once it is attached to the first medical device 100 is designed to be easily and quickly attached and detached to a second medical device, normally only requiring the use of one hand. Furthermore, the button 310 and the one not shown allows the second medical device to be easily coupled and decoupled from the first medical device 100 if the need arises for the second medical device to be operated by a different user without having to disengage the second medical device from the jaws of the clamp. This is accomplished by snapping the housing 304 to the rack-type joint 302 to attach the second medical device and then pressing the buttons to release the second medical device. The rack-type joint 302 may further include a box 309 in the interior thereof. The box 309 may have a first rod 311 and a second rod 313 rotatably placed on the opposite sides of the box 309 and at the front of the box 309, the function of which will be described below.

The housing 304 supports the pincer device 303 on one side thereof. The housing 304 includes the aperture 330 on the top wall of the housing and aperture 331 on the bottom wall of the housing 304. Both apertures are in vertical alignment to accept a retaining pin (not shown) that acts as a pivot for a first jaw 312 and a second jaw 314. A handle for manually applying pressure may be connected to each jaw, Jaw 312 has handle 330. Jaw 314 has handle 332. Each jaw may have structure to act as a fulcrum comprising an upper and lower ear with an aperture. Each jaw may also possess an extension behind the fulcrum to act as a lever. Jaw 312 has lower ear 320 and upper ear 322 connecting the arcuate portion to the extension 333. Extension 333 and handle 330 are on the opposite side of the fulcrum ears 320 and 322 to be able to apply leverage to the jaw 312. Jaw 314 has lower ear 328 and upper ear 326 connecting the arcuate portion to the extension 329. Extension 329 and handle 332 are on the opposite side of fulcrum ears 326 and 328 to be able to apply leverage to the jaw 314. Ears 326 and 328 are alternately engaged with the corresponding ears 320 and 322 of jaw 312. Apertures are provided in each of the ears 320 and 322 of jaw 312 and the ears 326 and 328 of jaw 314 so that a retaining pin can be positioned within them to further engage with the apertures 330 and 331 of the housing 304, thus allowing jaws 312 and 314 to pivot at the retaining pin. The upper ear 326 of jaw 314 includes a skirt having a raised circumference, and the lower ear 320 of jaw 312 includes a similar skirt so as to allow coil spring 318 to be placed within skirt of ear 326 and coil spring 316 within skirt of ear 320. Alternate embodiments may eliminate the coil springs 316 and 318 and have flat leaf springs or resilient, but flexible, materials to serve as the biasing device biasing the jaws 312 and 314 together, Springs 316 and 318 have straight runs at the ends at about right angles to each other. Skirts of ears 326 and 320 include a slit 327 made in the skirt so as to anchor one end of the spring. The other end of the spring extends over and outside the skirt and is placed against structure on the inside of housing 304, For example, spring 318 fits within skirt of ear 326, and a straight end of spring 318 fits into slit 327, and the other end of spring 318 extends above the skirt and abuts against the inside of the housing 304 at a suitable place to act as an anchor for the spring 318. Spring 316 is likewise placed in jaw 312. Thus, springs 316 and 318 maintain jaws 312 and 314 normally closed. Depressing handles 330 and 332 counteracts the spring forces, allowing jaws 312 and 314 to be opened to allow a second medical device to be placed therein. When housing 304 with pincer 303 is slid onto rack-type joint 302, the extension 333 passes on the outside of the rod 311 of box 309 and the extension 329 passes on the outside of the rod 313 so as housing 304 is pressed against the rack-type joint 302, the extensions 333 and 329 are spread apart or at least are forced apart to close jaws 312 and 314 more securely.

In other embodiments, the first and second jaws can be joined to each other via a flexible, but resilient hinge material to eliminate the need for springs and pivoting pins. Such embodiment may resemble the jaw structure illustrated in FIG. 1A. The inside surfaces of the jaws 312 and 314 may be covered by means to enhance the gripping strength between the jaws and the medical device. For example, the surfaces can have means to enhance gripping, including a soft, pliable material, a sticky or tacky material such as a releasable adhesive, magnets, keyed features (i.e., components that fit within other slots or notches), VELCRO®, surface roughening, and/or additional material wrapped around the catheter.

Figure 4A:
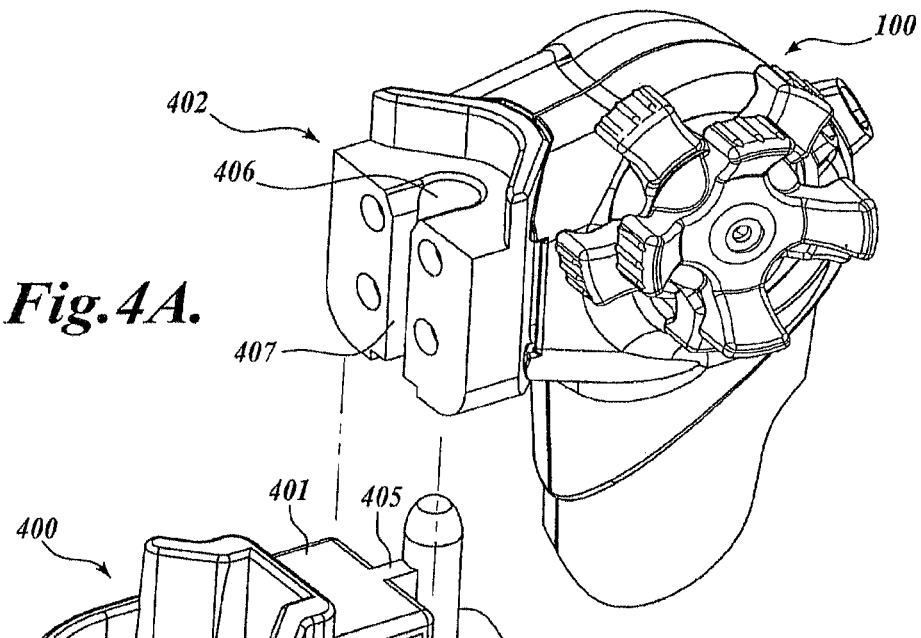
FIGS. 4A-4C are diagrammatical illustrations of an apparatus to attach a first medical device to a second medical device in accordance with another embodiment of the present invention.
Figure 4B:
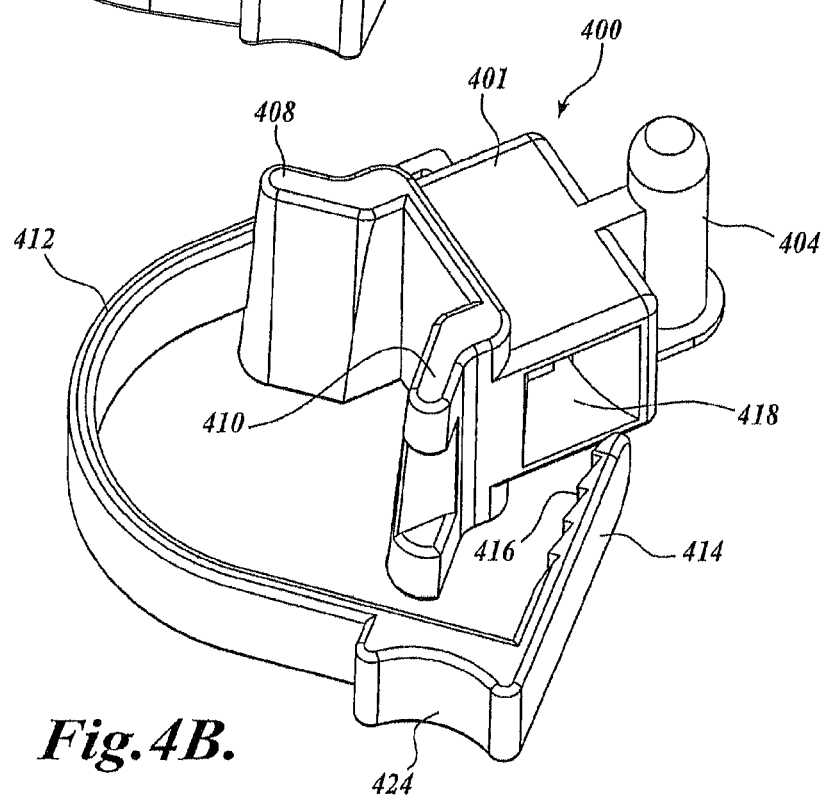

Referring to FIGS. 4A-4B, another embodiment of an apparatus 400 is illustrated for attaching a first medical device to a second medical device. The apparatus 400 may include a base component 402 and a wire tie component 400. The base 402 is illustrated being attached to the medical device 100. Attachment of base 402 to medical device 100 may be via mechanical fasteners, for example. Base 402 may comprise an aperture 406 disposed vertically on the base 402 and centrally located between the sides of the base 402, The aperture 406 may be connected to a slot 407 also extending vertically on the base 402 and on the side of the base 402 that is opposite to the medical device 100.

The wire tie component 400 may include a buckle 401. The buckle 401 may be a box-like structure having a top and bottom wall, a back wall, and a front wall that extends beyond the top and bottom walls. The buckle 401 includes first 408 and second 410 walls placed at an angle on the front wall to support the second medical device. Finally, the buckle 401 has a side wall, but the opposite side of the buckle 401 is generally open, the purpose of which will be described below. The back wall of the buckle 401 may support an upwardly-pointing post 404 attached via web 405 that fits within the aperture 406 and slot 407 on the base 402. The buckle 401 may include a flexible strap 412 that is connected to one side wall of the buckle 401. The strap 412 may be flexible such that the strap 412 can be bent around from one side of the buckle 401 to the other to hold a second medical device to the buckle 401. The strap 412 may include a tip 414 having serrations 416 on the end opposite to the end of the strap 412 that is attached to the buckle 401. The tip 414 may be placed at a right angle to the remainder of the strap 412. The strap 412 includes a button 424 that may be placed by the tip 414 and may be integrally molded to the strap 412. The strap 412 may loop around the second medical device, so that the tip 414 of the strap 412 may be inserted into the buckle 401 on the side of the buckle 401 that is generally open but includes a receiving guide 418 to guide the tip 414 into the buckle 401 in a desired location.

Figure 4C:
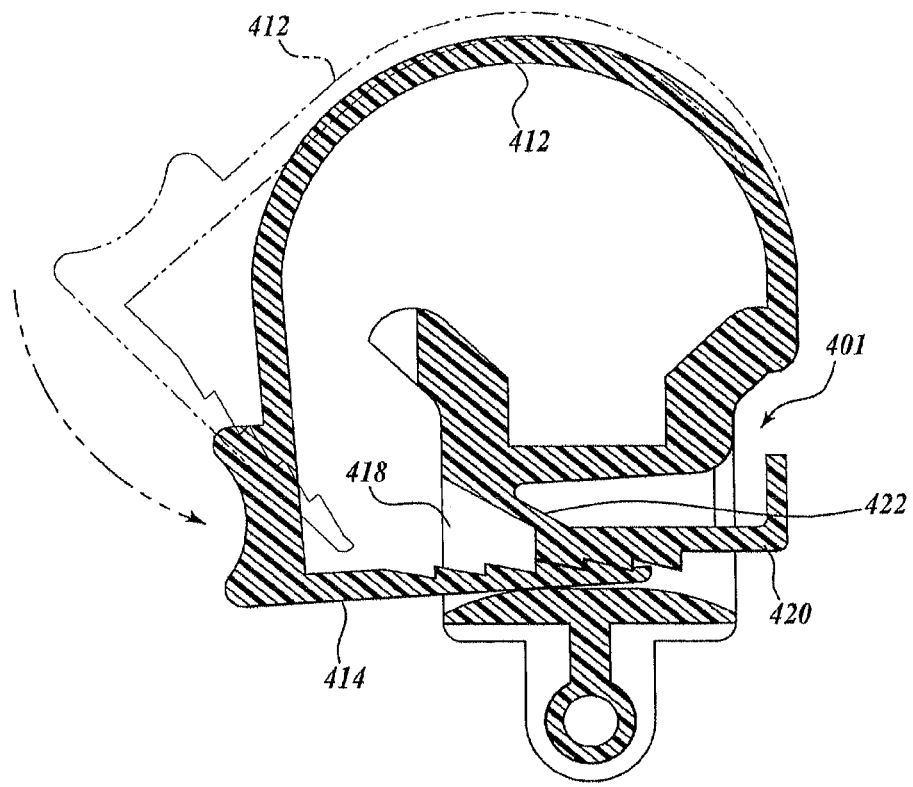

Referring specifically to the cross-sectional illustration of FIG. 4C, the strap 412 (also shown in phantom) may be looped around so that the tip 414 is inserted within the receiving guide 418 of the buckle 401 on the open side of the buckle 401. A tab 420 is supported by a wall also supporting the fixed end of the strap 412. The connection between the tab 420 and the wall is flexible and acts as a hinge 422 that allows the tab 420 to reciprocate up and down as serrations on the tip 414 slide by. The tab 420 includes serrations that face in the opposite direction as the serrations of the tip 414, Thus, the tip 414 can be locked in position with the tab 420.

The tip 414 may be released by application of pressure against a lever handle attached to the tab 420, which causes the serrations of the tab 420 to disengage with the serrations of the tip 414 and allows the strap 412 to disengage from the buckle 401 and release the second medical device.

In other embodiments, instead of the strap 412 having serrations at the tip 414, the strap 412 may have other joining members, such as a hook and loop fastener, snap buttons, or the like. The inside surface of the strap 412 may be covered by means to enhance the gripping strength between the strap and the medical device. For example, the surface can have means to enhance gripping, including a soft, pliable material, a sticky or tacky material such as a releasable adhesive, magnets, keyed features (i.e., components that fit within other slots or notches), VELCRO® surface roughening, and/or additional material wrapped around the catheter.

The apparatus once it is attached to the first medical device 100 is designed to be easily and quickly attached and detached to a second medical device, normally only requiring the use of one hand. Furthermore, the base 402 and post 404 allows the second medical device to be easily coupled and decoupled from the first medical device 100 if the need arises for the second medical device to be operated by a different user without having to disengage the second medical device from the strap 412. This may be accomplished by simply inserting the post 404 onto the base 402 and reversing the process to remove the second medical device.

Referring to FIGS. 5A-5D, an apparatus 500 for attaching a first medical device to a second medical device is illustrated. The apparatus 500 may include a base component 502 that may be attachable to a first medical device, such as medical device 100, and a clamp component 504. The base 502 may include a top plate 503 positioned orthogonal to the base 502. The top plate 503 may include a rectangular slot 506 at the distal side. Slot 506 acts as an anchor for a corresponding peg of the clamp component 504. The base 502 may include a spring 508. The spring 508 may include a flat strip of material formed as an S-curve of adequate width to accommodate a second slot 512 on the bottom leg of the S-curve of equal length as the slot 506 on the top plate 503. The upper leg of the S-curve may be attached perpendicular to the flat front surface of base 502 opposite to the side which is attached to the first medical device. The bottom leg of the S-curve is connected to a handle 510. The handle 510 can be depressed, thus, compressing the bottom leg of the S-curve and decreasing the distance between the first slot 506 and the second slot 512.

The clamp component 504 may include a bracket to removably secure the clamp to the first medical device. The bracket may include a top peg 514 attached to a sideways arm and a second bottom peg 516 attached to a sideways arm, each peg may be sized to enter into the respective first top slot 506 and the second bottom slot 512. Both arms that hold pegs 514 and 516 may extend sideways before turning up at the ends. The upper peg is pointed up and the bottom peg has a ramp and a ledge behind the ramp at the end of the peg. The upper peg 514 may be first engaged with the slot 506 from below the slot 506. The clamp component 504 pivots around the first top peg 514 so that the ramp at the end of the lower peg 516 strikes a ramp of opposite slope on the end of the bottom leg of the S-curve. Continued application of force causes the bottom leg of the S-curve to deform slightly upwards to allow the peg 516 to engage the slot 512. When the handle 510 is pushed up, the reduced distance releases the bottom peg 516 from slot 512, and thus, the clamp component 504 can be removed from the base 502. The apparatus once it is attached to the first medical device 100 is designed to be easily and quickly attached and detached to a second medical device, normally only requiring the use of one hand. Furthermore, the pegs 514 and 516 may allow the second medical device to be easily coupled and decoupled from the first medical device 100 if the need arises for the second medical device to be operated by a different user without having to disengage the second medical device from the jaws of the clamp 504 by simply operating the handle 510.

The clamp component 504 may include a first 518 and a second 520 jaw. The second jaw 520 supports the first and the second pegs described above, Each jaw has an arcuate portion followed by a straight portion. The first jaw 518 is connected to the second jaw 520 via a living hinge 522 after the arcuate portions and at the straight portions. Living hinge 522 may be a flexible strip of material that is narrower at the center to allow flexing of the jaws 518 and 520 to open or close. Jaws 518 and 520 continue as extensions 528 and 530 on the opposite side of the living hinge 522. First jaw 518 and second jaw 520 form a pincer device where living hinge 522 acts as a fulcrum and extensions 528 and 530 of jaws 518 and 520 behind the living hinge 522 act as levers that can be pressed nearer to each other to open the jaws or spread apart to close the jaws. For example, pressing the extensions 528 and 530 nearer to one another causes jaws 518 and 520 to open wider, while pushing extensions 528 and 530 apart closes the jaws 518 and 520. A locking mechanism includes a toggle joint.

Figure 5A:
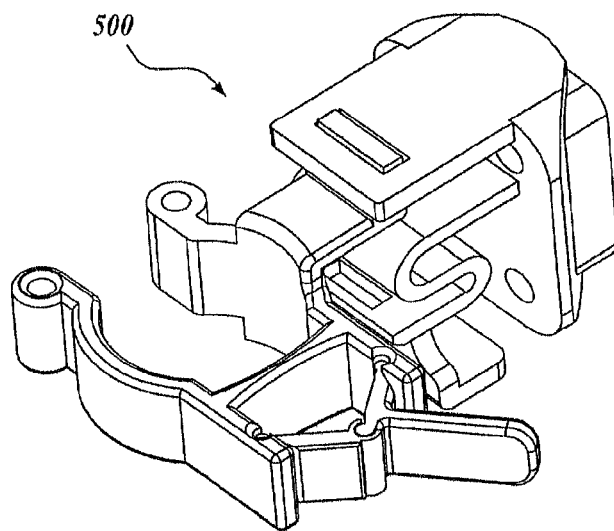
FIGS. 5A-5D are diagrammatical illustrations of an apparatus to attach a first medical device to a second medical device in accordance with another embodiment of the present invention.
Figure 5B:
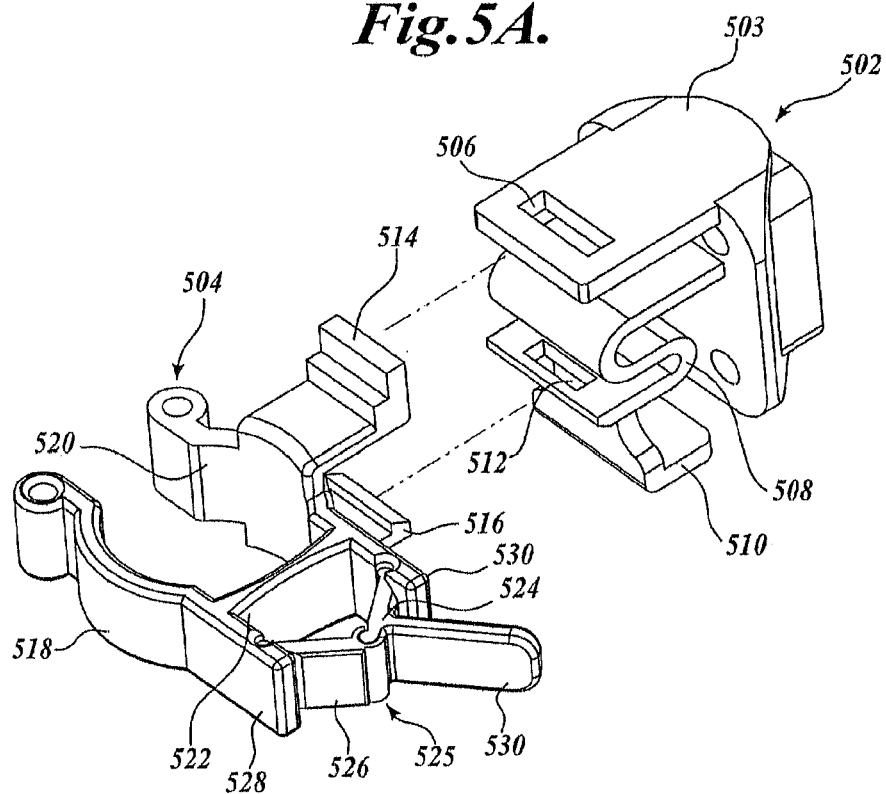
Figure 5C:
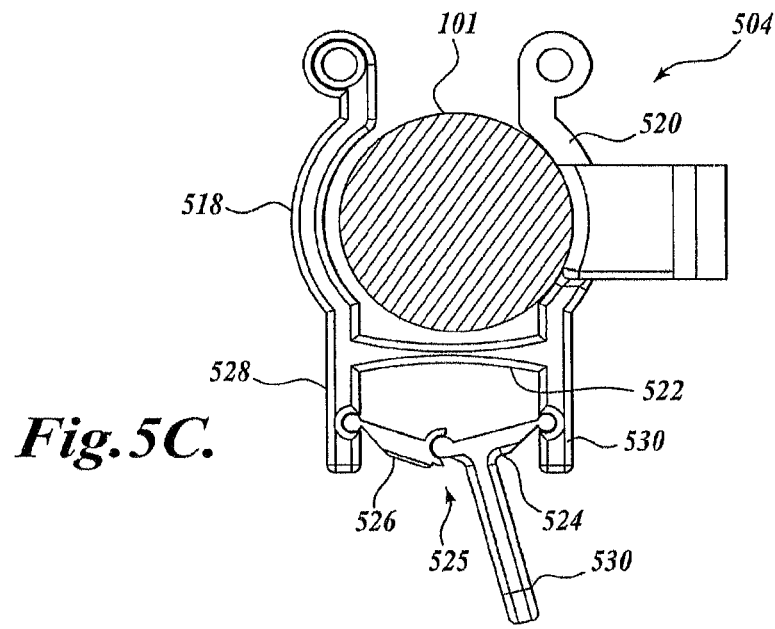
Figure 5D:
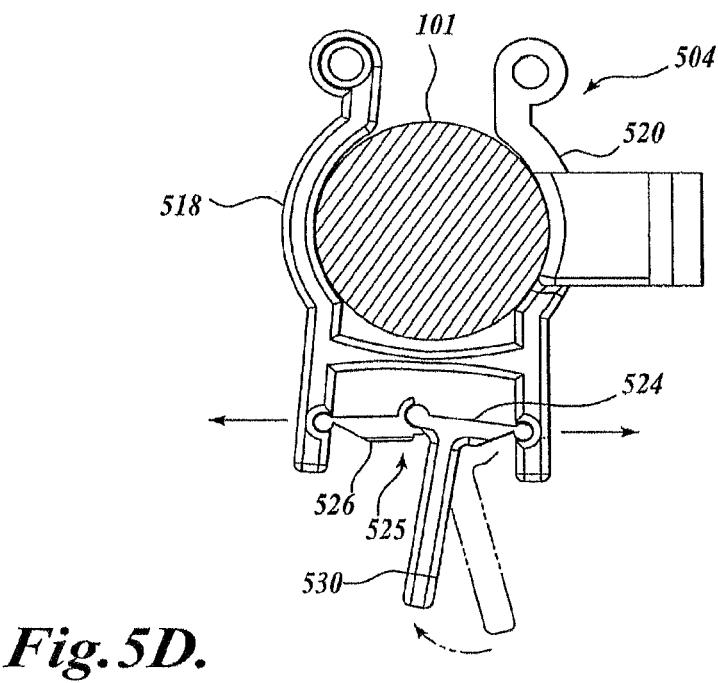

A toggle joint acts to push extensions 528 and 530 apart and, thus, to close the jaws. The toggle joint may be made from a first leg 526 and a second leg 528 joined to each other at about midway of the living hinge 522, resembling a knee 525. The combined length of leg 524 and leg 526 when straightened is greater than the length of the living hinge 522. When a force is applied to straighten the knee 525, the opposite ends of the legs 526 and 528 apply an outward force or push against the extensions 528 and 530 and close the jaws 518 and 520. The inner surfaces of the extensions 528 and 530 include a groove or socket, as best seen in FIGS. 5C and 5D, The sockets of the extensions 528 and 530 are each engaged with one leg of the toggle joint. The first leg 526 is pivotally attached to the inner surface of extension 528, The second leg 524 is pivotally attached to the inner surface of the extension 530, Both legs 526 and 524 are pivotally attached to each other at the knee 525, Leg 524 is connected to a lever 530 attached perpendicular to leg 524, Referring specifically to FIG. 5C, in a first position, the knee 525 juts outward and bends away from the hinge 522. This is the no-load configuration that allows the living hinge 522 to flex. When the knee 525 juts outward or bends away, there is no compressive force on legs 524 and 526 because there is no resistance against the jaws 518 and 520 opening. The inside surfaces of jaws 518 and 520 are shown slightly open and not fully pressing against the second medical device 101.

As seen in FIG. 5D, moving the lever 530 to the opposite side forces the knee 525 to straighten, which causes the extensions 528 and 530 to be spread further apart, eventually reaching the point where the knee 525 bends inwards and towards the hinge 522. This has the effect of closing the jaws 518, 520 around the second medical device 101. Resistance to moving the lever 530 will be felt when the jaws 518, 520 touch the second medical device 101, Continued movement of the lever 530 to the opposite side continually increases the separation distance between extensions 528 and 530 up to the point when the knee 525 is straight. Past this point, the knee 525 will jut inwards or bend towards the hinge 522 and release some of the pressure that is applied to the extensions 528 and 530. It is at this point that the knee 525 can be prevented from moving further as just after the knee 525 juts inward or bends towards the hinge 522, the toggle joint may apply close to the maximum pressure on the jaws 518, 520, This is the loaded configuration because the jaws 518 and 520 not being able to close further around the second medical device 101 places the legs 524 and 526 under tension that prevents the knee 525 from returning to the outward jutting configuration, Thus, the second medical device 101 is secured within jaws 518 and 520. The medical device 101 can be released by returning the lever 530 to the original position, as illustrated in FIG. 5C.

In alternate embodiments, the first and second jaws may be replaced by any of the jaw structures as illustrated in FIG. 1A, 2B, or 3B, The inside surfaces of the jaws 518 and 520 may be covered by means to enhance the gripping strength between the jaws and the medical device. For example, the surfaces can have means to enhance gripping, including a soft, pliable material, a sticky or tacky material such as a releasable adhesive, magnets, keyed features (i.e., components that fit within other slots or notches), VELCRO®, surface roughening, and/or additional material wrapped around the catheter.

Referring to FIGS. 6A-6C, an alternate embodiment of an apparatus 600 for attaching a first medical device to a second medical device is illustrated. The apparatus 600 may include a base 610 that can be mechanically connected to a first medical device. The base 610 may have a flat surface 611 on the side opposite from the mechanical connection to the medical device. The apparatus 600 may include a first jaw 602 and a second jaw 604 connected to one another via a joining wall 612, The jaws 602 and 604 extend behind the wall 612 into beams 614 and 616 that are rigidly connected to the surface 611 of the base 610, Each jaw 602 and 604 may be curved or bowed so that the placement of the jaws 602 and 604 with the bowed portions facing each other define a wide center area for accepting a second medical device and a narrow opening defined at or close to the ends of the jaws 602 and 604. A sliding ring 606 is supported within slots created in jaws 602 and 604 that allow the sliding ring 606 to be rotated in relation to the jaws 602 and 604. For example, the end of jaw 602 includes a slot through which the end of the sliding ring 606 is passed. The jaw 604 includes a slot that allows the opposite end of the sliding ring 606 to pass through. The sliding ring 606 includes a handle 608 on the end that allows rotating the sliding ring 606 within the slots of the jaws 602 and 604. As best seen in the cross-sectional illustrations of FIGS. 6B and 6C, the sliding ring 606 defines less than a complete circumference of a circle. The sliding ring 606 has a gap in its circumference that is generally proportionate to the opening between the first jaw 602 and the second jaw 604. As illustrated in FIG. 6B, the gap in the sliding ring 606 can be aligned with the opening between the jaws 602 and 604 to allow a medical device 101 to pass by the opening and be placed within the interior of the first and the second jaws 602 and 604, In FIG. 6C, the sliding ring 606 is illustrated being rotated via the handle 608. Thus, the end of the sliding ring 606 may close the opening between jaws 602 and 604, thereby retaining the second medical device within the jaws 602 and 604. The forward end of the sliding ring 606 may engage with the jaw 604 under pressure so that the jaws 602 and 604 apply a squeezing force on the medical device 101, To release the medical device 101, the handle 608 may be moved to the position shown in FIG. 6B, thus creating the opening between the jaws 602 and 604 once again to release the second medical device 101.

Figure 7A:
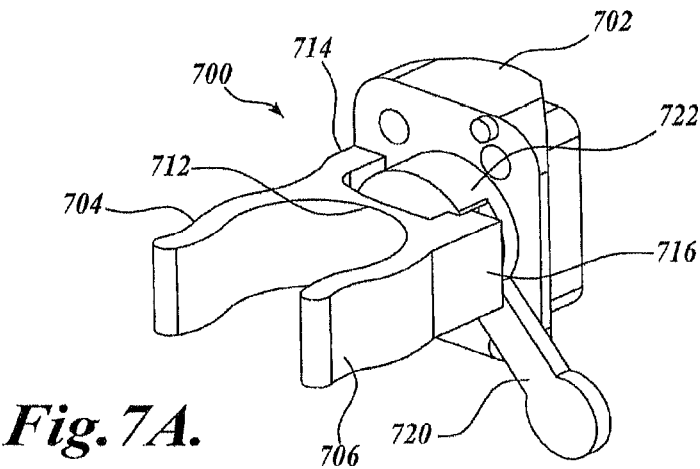
FIGS. 7A-7D are diagrammatical illustrations of an apparatus to attach a first medical device to a second medical device in accordance with, another embodiment of the present invention.
Figure 7B:
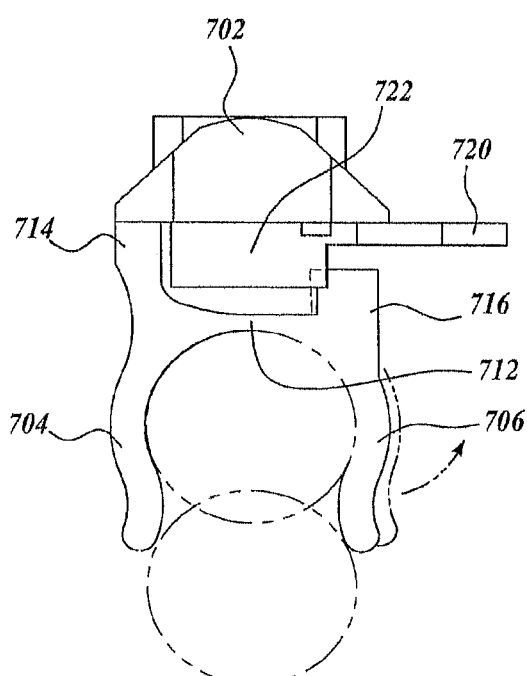

The inside surfaces of the jaws 602 and 604 and the sliding ring 606 may be covered by means to enhance the gripping strength between the jaws and the medical device. For example, the surfaces can have means to enhance gripping, including a soft, pliable material, a sticky or tacky material such as a releasable adhesive, magnets, keyed features (i.e., components that fit within other slots or notches), VELCRO®, surface roughening, and/or additional material wrapped around the catheter. For example, in one embodiment, the sliding ring 606 may have a smaller inside diameter than the inside diameter defined by the jaws 602 and 604. The sliding ring 606 may then engage with a corresponding groove or notch around the outer circumference of the medical device 101. Referring to FIGS. 7A-7D, an embodiment of an apparatus 700 for attaching a first medical device to a second medical device is illustrated. The apparatus 700 may include a clamp attached to a base 702, The base 702 may be attachable to a first medical device via any mechanical or adhesive means. The apparatus 700 may include a first jaw 704 and a second jaw 706 connected to each other via a flexible transverse wall 712. The interior surfaces of the jaw 704, wall 712, and jaw 706 combine to form an arcuate shape, such as a portion of a circle. The jaw 704 extends behind the wall 712 and forms a beam 714 that is connected to the surface of the base 702 on one side of the base 702. As appreciated from FIG. 713, the first jaw 704, the second jaw 706, and the intermediate wall 712 are joined to the base 702 via the beam 714 that extends from jaw 704. The opposite jaw 706 extends past the wall 712 and forms a block 716 having at least a straight edge facing inward. As depicted in FIG. 7B, when a second medical device is pressed against the opening defined by the ends of the jaws 704 and 706, jaws 704 and 706 will spread apart, allowing the second medical device to be captured within the jaws 704 and 706, Jaw 706 may experience most of the movement as intermediate wall 712 may flex to allow jaw 706 to open. Once within jaws 704 and 706, the medical device can be locked in position by a locking mechanism.

A locking mechanism may include a disk 722 that is rotationally attached to the base 702. The disk 722 is positioned between the base 702 and the intermediate wall 712 and attached to the base 702 at its center via a pivot pin to allow rotation of the disk 722. The disk 722 defines a earning surface on the side of the disk 722 and formed from the outer circumference of the disk 722. The raining surface may include a first cut-out 724 and a second cut-out 726 formed from reduced thickness areas of the disk 722. The first cut-out 724 may define a straight edge that cuts the disk 722 along a chord of a circle close to the circumference of the disk 722. The second cut-out 726 may define a second straight edge that cuts the disk 722 along a chord of a circle that is farther away from the circumference of the disk 722. The straight edge of cut-out 724 and the straight edge of cut-out 726 may be positioned at right angles to each other, and a transition between them may comprise a rounded corner. The cam surface therefore includes an edge of varying thickness along the perimeter of the disk 722 and on the side of the disk 722.

Figure 7C:
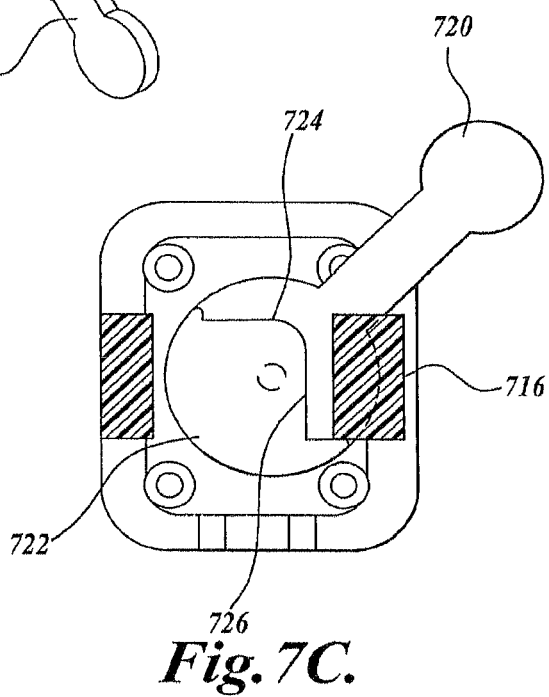
Figure 7D:
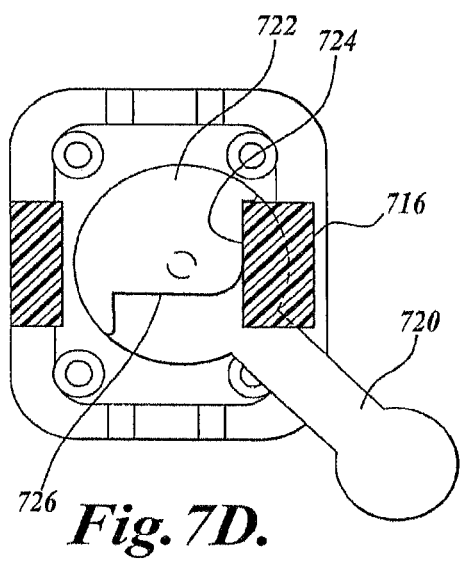

Referring to the cross-sectional illustration of FIG. 7C, the block 716 is shown in position within the cut-out 726 so that the straight edge of the block 714 may be generally parallel to the straight edge of the out-out 726. There may be a gap between the edge of the block 716 and the edge of the cut-out 726 and, thus, allows the jaw 706 to which block 716 is attached to be flexed as described above. Referring to FIG. 7D, the handle 720 attached to the disk 722 may be moved to rotate the disk 722 so that the edge of the out-out 724 lies generally parallel and touching or very nearly touching the straight edge of the block 716, and may even have pressed against the block 724 with a slight force so as to put pressure on the jaw 706. As can be appreciated, the block 716 has little to no room to flex to the side because of the nearness of the straight edge of the out-out 724 against the block 716. Thus, in the configuration shown in FIG. 7D, the jaw 706 is prevented from opening. Therefore, the second medical device is securely held within jaws 704 and 706 illustrated in FIG. 7D, The inside surfaces of the jaws 704 and 706 may be covered by means to enhance the gripping strength between the jaws and the medical device. For example, the surfaces can have means to enhance gripping, including a soft, pliable material, a sticky or tacky material such as a releasable adhesive, magnets, keyed features (i.e., components that fit within other slots or notches), VELCRO®, surface roughening, and/or additional material wrapped around the catheter.

Figure 8A:
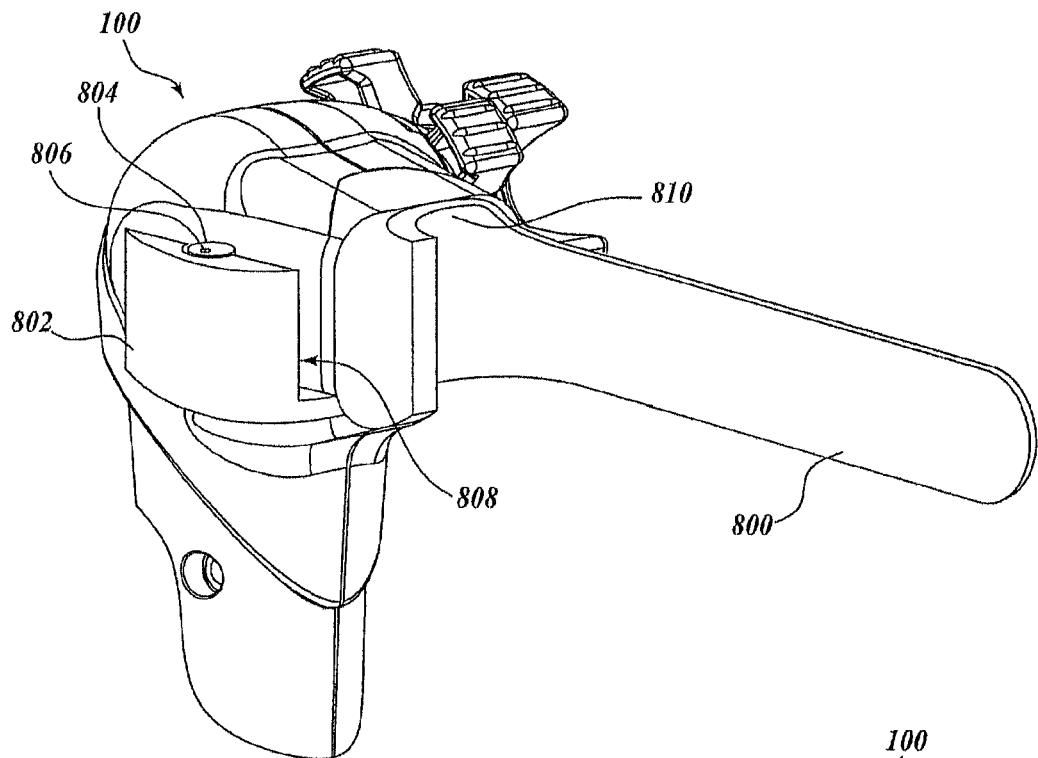
FIGS. 8A-8B are diagrammatical illustrations of an apparatus to attach a first medical device to a second medical device in accordance with another embodiment of the present invention.
Figure 8B:
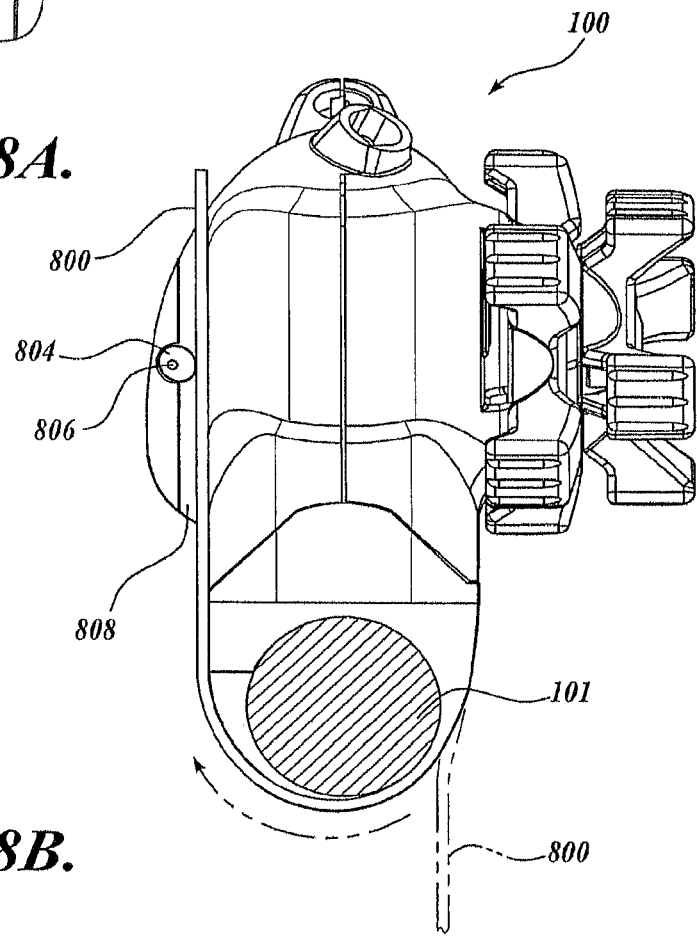

Referring to FIGS. 8A and 8B, an embodiment of an apparatus for attaching a first medical device to a second medical device is illustrated. The first medical device 100 may include a flexible strap 800 attached on one side of the medical device 100. Next to the strap 800 is a receptacle 808 for receiving a second medical device. Receptacle 808 can be an indentation that conforms to the shape of the second medical device. The medical device 100 may include structure 802 having a slot 808 that is provided on the side of the medical device that is opposite to the side on which the strap 800 is attached. Slot 808 extends from a forward opening to a rear opening to allow strap 800 to pass therethrough from front to back. A cylindrical earn 804 positioned on one side in the path through the slot 808 has a pivoting pin 806 placed off-center in the cam 804 so that upon rotation of the cam 804, the earn 804 will cause a narrowing or constriction of the slot 808 between the cam's 804 surface and the opposite side of the slot 808, The strap 800 can be wrapped around a second medical device 101, as best seen in FIG. 8B, The strap 800 has a free end which is inserted through the slot 808 between the first medical device 100 and the off-center cam 804. The cam 804 can have serrations or pyramid-like projections on the surface to "bite" against the strap 800. Thus, when the end of the strap 800 is inserted within the slot 808, the end of the strap 800 pivots the cam 804 to align the narrow portion of the cam 804 next to the slot 808 to have adequate width for passage of the strap 800 through the slot 808, When the direction of the strap 800 is reversed, such as when the strap 800 is pulled, the cam 804 pivots so that the wider part of the cam 804 is turned to face the slot 808, thus narrowing the width of the slot 808 next to the earn 804 that causes the cam 804 to wedge itself against the strap 800. In use, the strap 800 may first be pulled tight against the second medical device 101. When the strap 800 is released, the cam 804 bites against the strap 800, thus preventing the strap 800 from releasing. As alternatives to an off-center cam, the can can have an eccentric lobe or the cam can travel along a widening guide where the slot is widest when the cam travels down the guide and the slot is narrowest when the cam is closest to the front of the guide.

The inside surface of the strap 800 may be covered by means to enhance the gripping strength between the strap and the medical device. For example, the surface can have means to enhance gripping, including a soft, pliable material, a sticky or tacky material such as a releasable adhesive, magnets, keyed features (i.e., components that fit within other slots or notches), VELCRO®, surface roughening, and/or additional material wrapped around the catheter.

Figure 9:
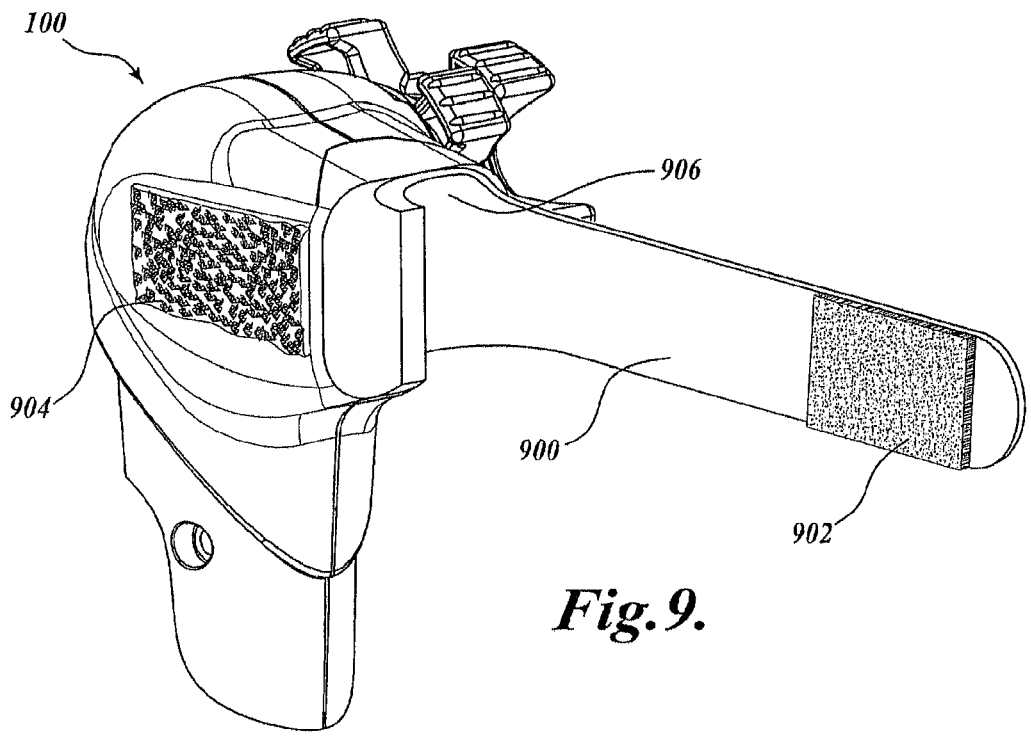
FIG. 9 is a diagrammatical illustration of an apparatus to attach a first medical device to a second medical device in accordance with another embodiment of the present invention.

Referring to FIG. 9, an embodiment of an apparatus for attaching a first medical device to a second medical device is illustrated. The medical device 100 may include a flexible strap 900 attached to one side of the medical device, A receptacle 906 in the first medical device may be positioned adjacent to the strap 900 to accommodate a second medical device, Receptacle 906 may be an indentation that conforms to the shape of the second medical device. The strap 900 may have a free end that includes either the loop or hook portion of a hook-and-loop fastener. The corresponding portion of the hook-and-loop fastener may be attached to the side of the medical device 100 that is opposite to the side on which the strap 900 is attached. A second medical device may be placed within the receptacle 906. A length of the strap 900 is wrapped around the second medical device and the free end of the strap 900 is secured to the opposite side of the first medical device. For example, the free end of the strap 900 may have the hook portion of the hook-and-loop fastener 902, which is engaged to the loop portion 904 of the hook-and-loop fastener on the opposite side of medical device 100, thereby attaching the first medical device 100 to the second medical device (not shown).

The inside surface of the strap 900 may be covered by means to enhance the gripping strength between the strap and the medical device. For example, the surface can have means to enhance gripping, including a soft, pliable material, a sticky or tacky material such as a releasable adhesive, magnets, keyed features (i.e., components that fit within other slots or notches), VELCRO®, surface roughening, and/or additional material wrapped around the catheter.

Figure 10:
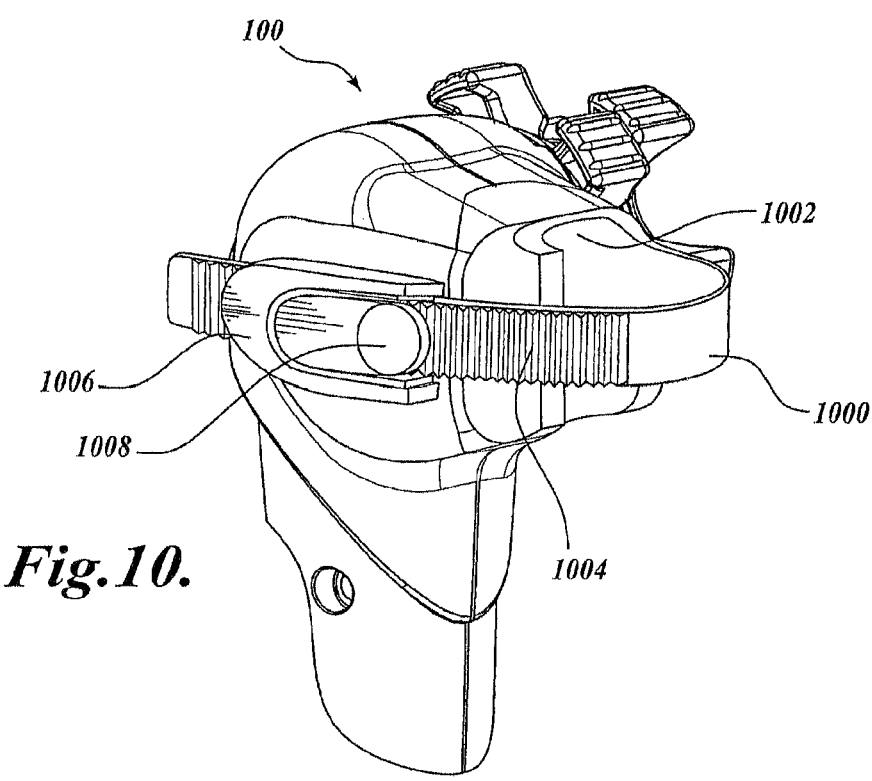
FIG. 10 is a diagrammatical illustration of an apparatus to attach a first medical device to a second medical device in accordance with another embodiment of the present invention.

Referring to FIG. 10, an embodiment of an apparatus for attaching a first medical device to a second medical device is illustrated. The medical device 100 includes a flexible strap 1000 attached on one side of the medical device 100. A receptacle 1002 may be placed adjacent to the strap 1000 to receive a second medical device (not shown). Receptacle 1002 may be an indentation that conforms to the shape of the second medical device. The strap 1000 may include a free end having serrations 1004 on one side of the strap 1000. The free end of the strap 1000 is inserted into a ratchet and pawl mechanism, which can be used to tighten a length of the strap 1000 around the second medical device. The ratchet 1006 may have serrations that engage with the serrations on the strap 1000, while the pawl 1008 prevents the strap 1000 from reversing direction. Application of pressure to the opposite side of the pawl 1008 releases the pawl 1008 from the strap 1000.

The inside surface of the strap 1000 may be covered by means to enhance the gripping strength between the strap and the medical device. For example, the surface can have means to enhance gripping, including a soft, pliable material, a sticky or tacky material such as a releasable adhesive, magnets, keyed features (i.e., components that fit within other slots or notches), VELCRO®, surface roughening, and/or additional material wrapped around the catheter.

Referring to FIGS. 11A-11C, an embodiment of an apparatus for attaching a first medical device to a second medical device is illustrated. The apparatus may include an over-center clamp 1100 and a base 1102 that may be mechanically fastened on one side to a first medical device. The base 1102 has a surface provided opposite to the medical device to support a first jaw 1102 and a second jaw 1104. The jaw 1102 is supported by and pivots on hinge 1106. The jaw 1104 is supported by and pivots on hinge 1104. The jaw 1102 extends past the hinge 1106 into a boss 1112. The jaw 1104 extends past the hinge 1108 into a boss 1114. The bosses 1112 and 1114 are arranged to create over-center action to lock the second medical device 101 in place. As best seen in FIG. 1113, when the jaws 1102 and 1104 are opened, the bosses 1112 and 1114 are not touching each other. As a medical device 101 is being pushed against the rear of the jaws 1102 and 1104 and bosses 1112 and 1114, the jaws 1102 and 1104 begin to close and the bosses 1112 and 1114 approach one another and may eventually touch. After the bosses 1112 and 1114 make contact with one another, resistance may be felt to further pushing of the medical device. However, increasing the application of pressure on the medical device 101 overcomes the resistance. When the bosses 1112 and 1114 cross the point where, because of the pivoting nature of the bosses, the bosses are no longer being pushed against each other and have crossed the center and are beginning to separate from one another, the bosses gradually release some of the stored tension, and it is at this point that because of the reversal of forces and the separation of the bosses 1112 and 1114, the jaws 1102 and 1104 are forced against the medical device 101 so that the jaws 1102 and 1104 hold the medical device 101 in place. Removal of the medical device 101 is effected by overcoming the resistance to pushing the bosses 1112 and 1114 closer to each other over the center, but in the opposite direction, until and because of the pivoting nature, the bosses will begin to separate and release the medical device 101.

The inside surfaces of the jaws 1102 and 1104 may be covered by means to enhance the gripping strength between the jaws and the medical device. For example, the surfaces can have means to enhance gripping, including a soft, pliable material, a sticky or tacky material such as a releasable adhesive, magnets, keyed features (i.e., components that fit within other slots or notches), VELCRO®, surface roughening, and/or additional material wrapped around the catheter.

Figure 12B:
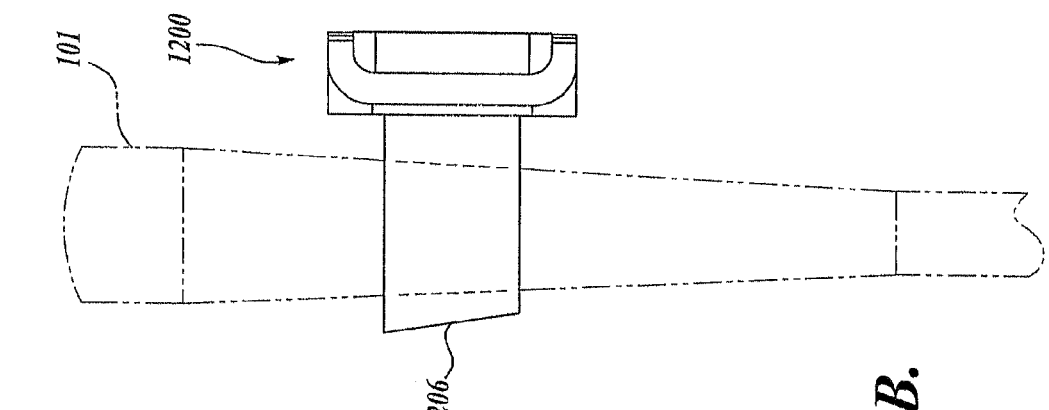
FIGS. 12A-12B are diagrammatical illustrations of an apparatus to attach a first medical device to a second medical device in accordance with another embodiment of the present invention.
Figure 12A:
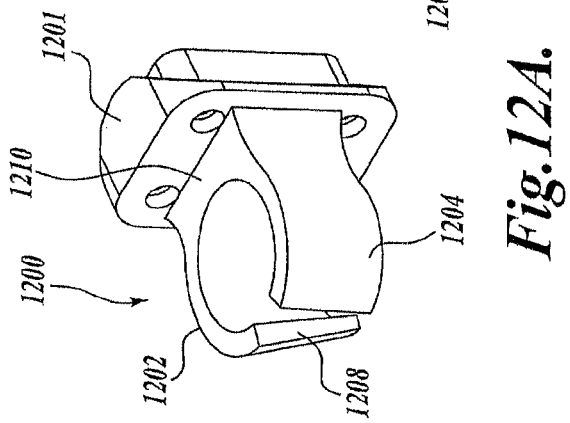

Referring to FIGS. 12A and 12B, an embodiment of an apparatus 1200 for attaching a first medical device to a second medical device is illustrated. The apparatus may include a funnel shaped clamp 1200 and friction to hold a medical device. The clamp 1200 includes a base 1201 that can be mechanically connected to a first medical device. The funnel shaped clamp 1200 may include a first jaw 1202 and a second jaw 1204, Both jaws are connected to an intermediate wall 1210 that is then attached to the surface of the base 1202. The jaws 1202 and 1204 terminate at an opening 1208. A cross-sectional profile taken of either of the jaws 1202 and 1204 along any of the length of the jaw will reveal an angled profile, as best seen in FIG. 12B, Thus, the radius of curvature of the jaws 1202 and 1204 is greatest at the highest elevation, and diminishes as the elevation decreases. Jaws 1202 and 1204 are formed from a semi-rigid material that may generally be stiff, but can give and flex. As best seen in FIG. 12B, a second medical device 101 is inserted between the first jaw 1202 and the second jaw 1204. Opening 1208 defined by the ends of the jaws 1202 and 1204 allows a narrow portion of the second medical device, such as an elongated shaft to squeeze through the opening 1208, while the handle of the second medical device 101, being formed as a gradually increasing circular object to closely match the angled profile of the jaws, is received between the jaws 1202 and 1204. The second medical device 101 is lowered and may be pressed downwardly, thereby applying pressure to the interior surfaces of the jaws 1202 and 1204, which may give a little by expanding outward, Friction and the force of the jaws 1202 and 1204 pressing against the second medical device 101 may prevent the medical device 101 from inadvertently being detached from the clamp 1200 and the first medical device.

The inside surfaces of the jaws 1202 and 1204 may be covered by means to enhance the gripping strength between the jaws and the medical device. For example, the surfaces can have means to enhance gripping, including a soft, pliable material, a sticky or tacky material such as a releasable adhesive, magnets, keyed features (i.e., components that fit within other slots or notches), VELCRO®, surface roughening, and/or additional material wrapped around the catheter.

Figure 13:
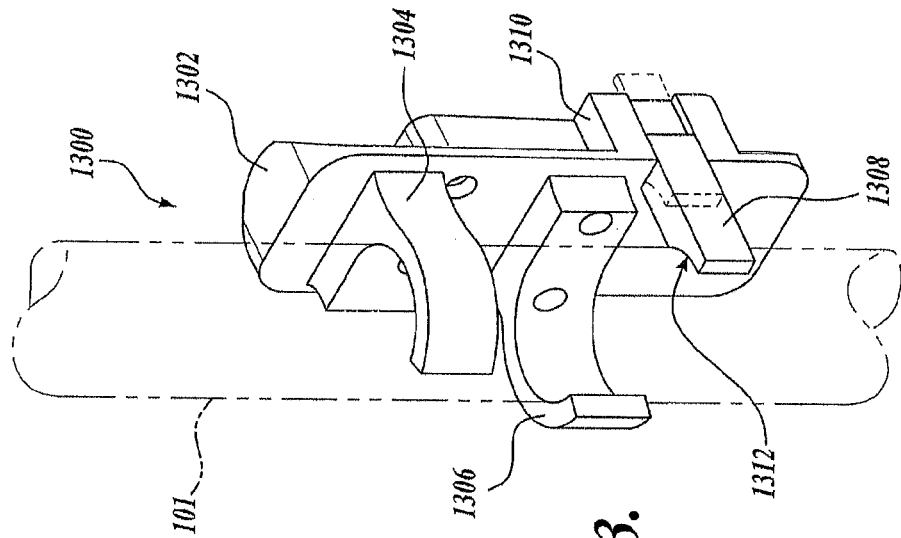
FIG. 13 is a diagrammatical illustration of an apparatus to attach a first medical device to a second medical device in accordance with another embodiment of the present invention.

Referring to FIG. 13, an apparatus 1300 for attaching a first medical device to a second medical device is illustrated. The apparatus 1300 may include a base 1302 that is mechanically or otherwise connected to a first medical device. The base 1302 may extend lengthwise along the medical device to accommodate at least two alternately positioned hooks 1304 and 1306 that may be placed on the base at different elevations such that the ends of the hooks face inwardly but, are not in alignment with respect to elevation. Hook 1304 is higher in elevation on the base 1302 compared to hook 1306, Hooks 1304 and 1306 may be rigidly attached to the surface of the base 1302, Hooks 1304 and 1306 may be formed from a semi-rigid material that may be generally stiff, but can give and flex. The base 1302 includes a latch mechanism 1308 that may be placed at a lower elevation than either of hooks 1304 and 1306. Latch mechanism 1308 may travel laterally with respect to the alignment of the base 1302 and within a guide 1310 on the base 1302. Latch mechanism 1308 may include an arcuate surface 1312 having a radius of curvature similar to hooks 1306 and 1304. The arcuate surface 1312 is directed inward and faces toward the lower hook 1306 so that the latch is aligned in the same direction as hook 1304, Latch mechanism 1308 acts as a third hook, similar to hook 1304, when latch mechanism 1308 is moved forward, thereby locking the second medical device 101 from opposite sides within the grasp of the first and second hooks 1304 and 1306 and further held by the latch mechanism 1308. Latch mechanism 1308 can then be moved to the rear, thus releasing the second medical device 101.

Figure 14A:
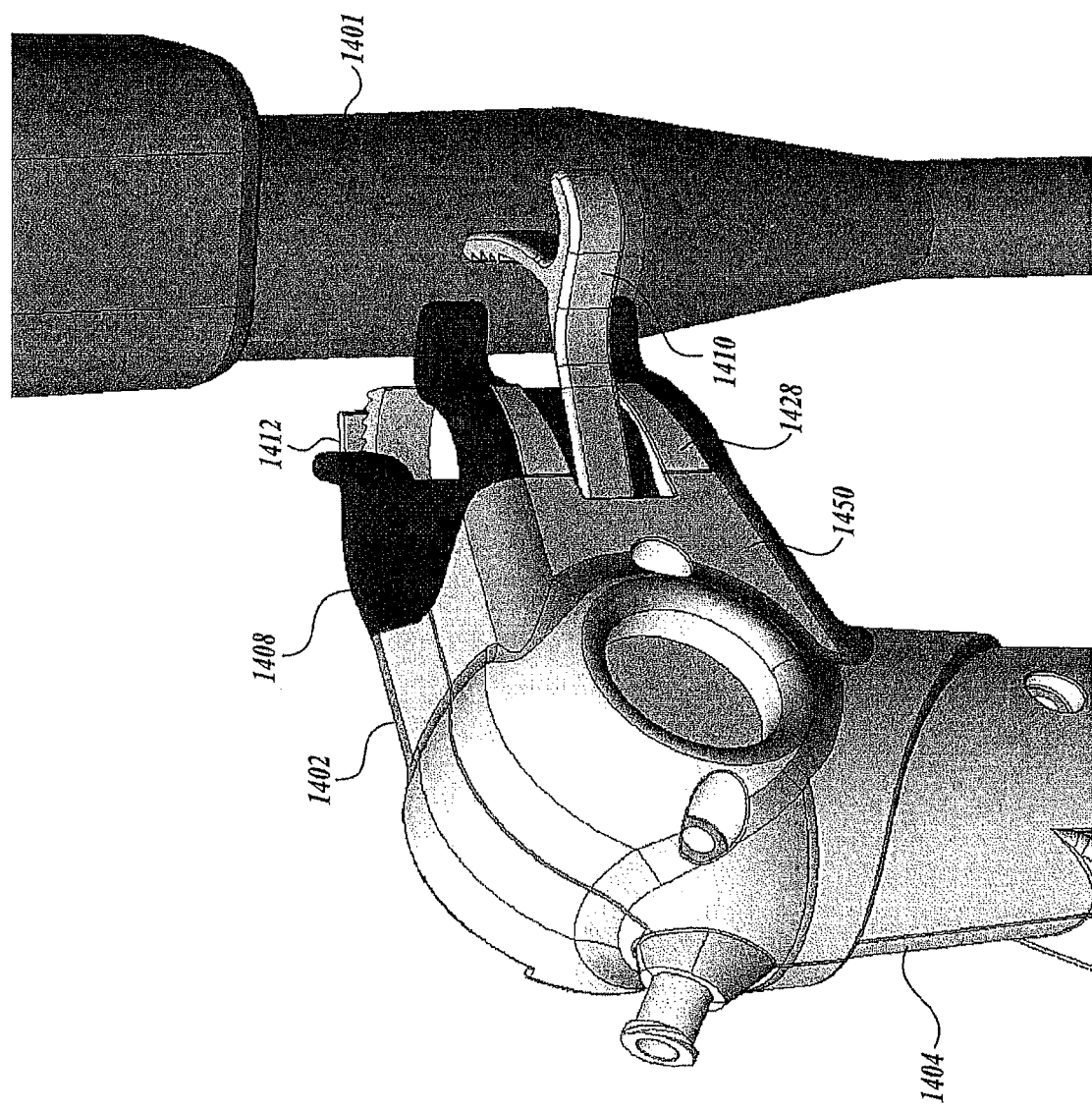
FIGS. 14A-14D are diagrammatical illustrations of an apparatus to attach a first medical device to a second medical device in accordance with another embodiment of the present invention.
Figure 14B:
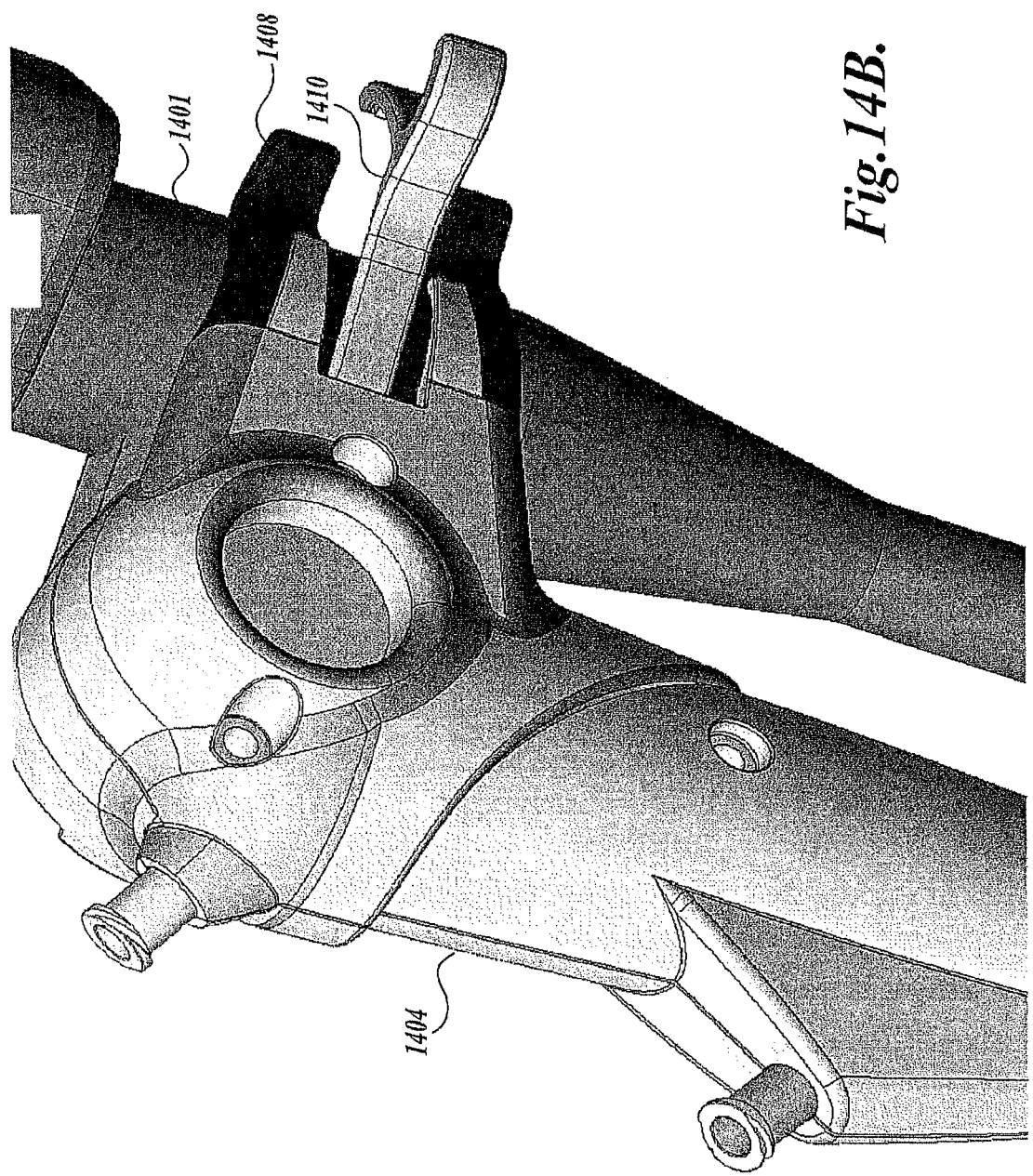
Figure 14C:
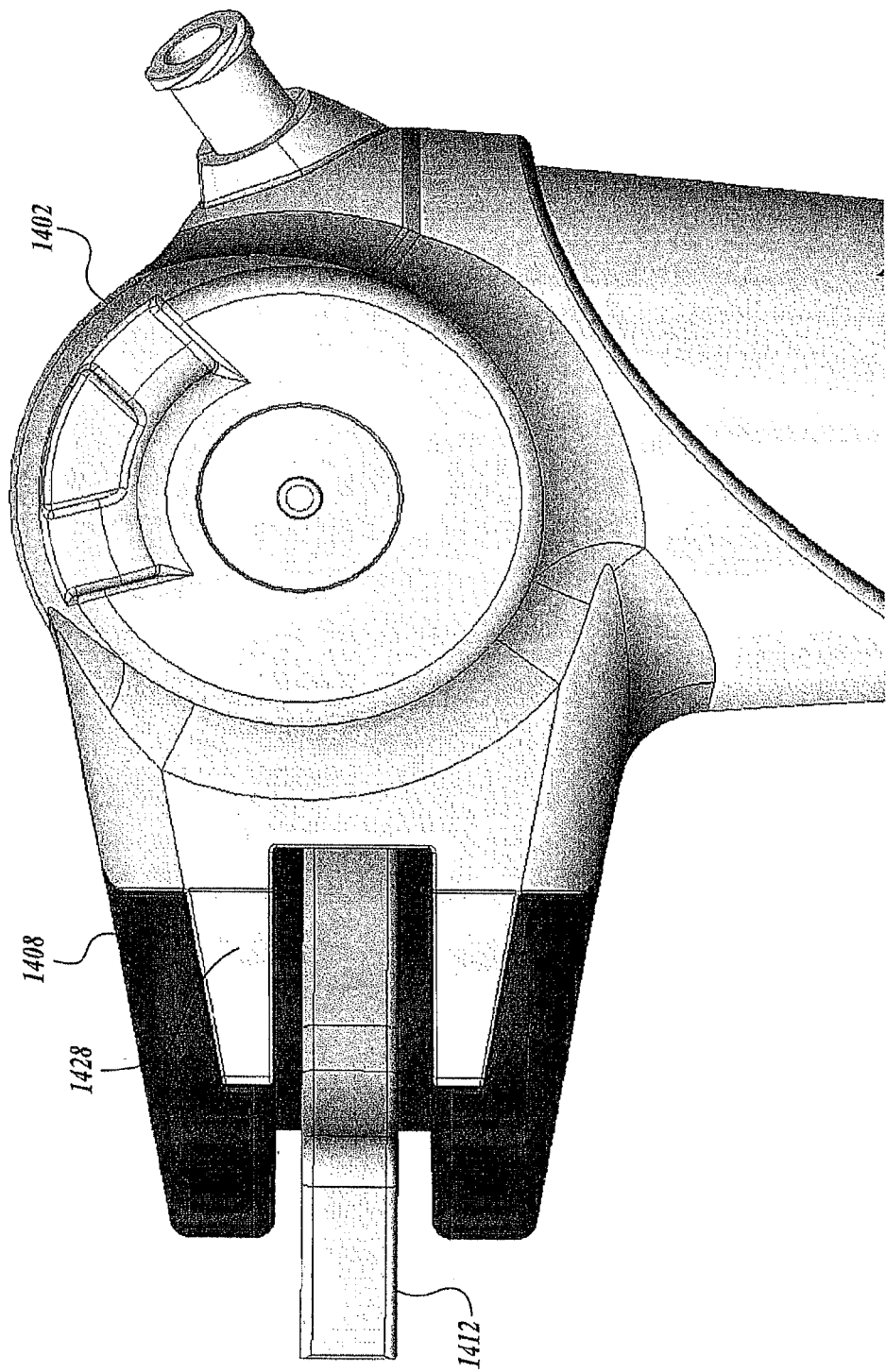
Figure 14D:
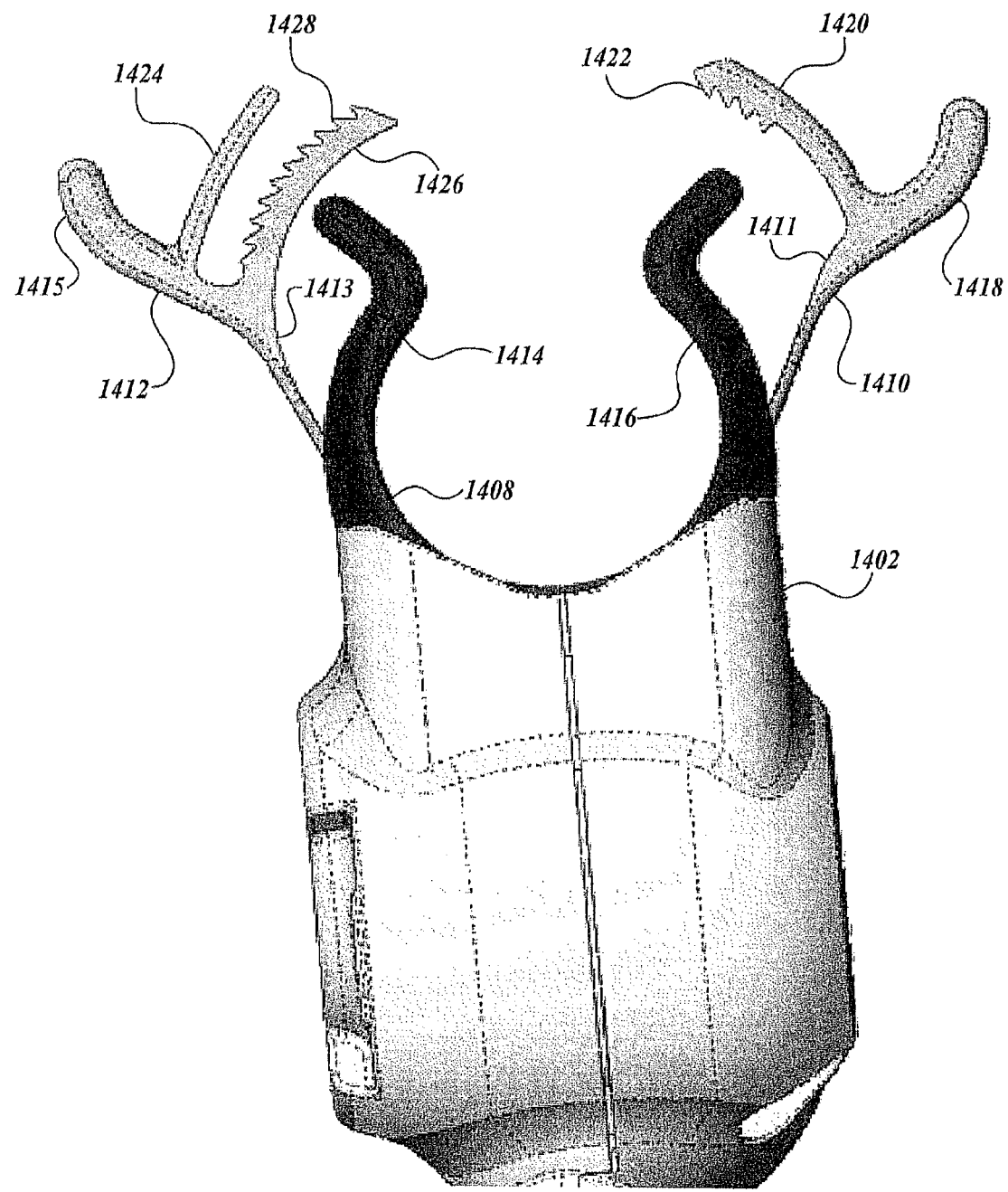

Any number of hooks can be positioned so as to face toward the inside, but placed on opposite sides with respect to an imaginary line along the center of the base. Furthermore, the latch can be located above, below or in between an upper and lower hook. The inside surfaces of the hooks 1304 and 1306 and of the latch 1308 may be covered by means to enhance the gripping strength between the hooks and latch and the medical device. For example, the surfaces can have means to enhance gripping, including a soft, pliable material, a sticky or tacky material such as a releasable adhesive, magnets, keyed features (i.e., components that fit within other sloth or notches), VELCRO®, surface roughening, and/or additional material wrapped around the catheter, Referring to FIGS. 14A-14D, an apparatus 1402 for attaching a first medical device 1404 to a second medical device 1401 is illustrated. The attachment of the apparatus 1402 to the medical device 1404 can be via any mechanical fastener or an adhesive. The apparatus 1402 includes a base 1450 which is attached to the medical device 1404, From the base 1450, one or more support beams 1428 extend away and generally perpendicular to the long axis of the medical device 1404. Support beams can be defined as upper lateral, upper medial, lower lateral, and lower medial. Each pair of support beams on either the lateral or medial side includes a first upper and a second lower support beam, which define a slot therebetween the first upper support beam and the second lower support beam. The upper lateral and medial support beams have an arcuate shape facing inwardly toward each other. The lower lateral and medial support beams have an arcuate shape facing inwardly toward each other. An elastomeric material 1408 is provided within the inner perimeter of the support beams, the function of which is to "hug" the second medical device 1401, As best seen in FIG. 14D, the elastomeric material 1408 includes two opposite, but similar holders 1414 and 1416, The apparatus 1402 may include a first set of upper holders 1414 and 1416 and a second set of holders that are not shown in FIG. 14D, but are beneath the holders 1414 and 1416. In FIG. 14C, the bottom set of holders is illustrated. Each elastomeric holder can correspond to a support beam such that the slot between support beams is preserved. As viewed from above in FIG. 14D, each holder 1414 and 1416 is the mirror image of each other with respect to a central axis. Each holder 1414 and 1416 and the bottom set of holders has an inside arcuate shape, which comes to a narrow constriction and which then turn outward to receive the second medical device 1401, The set of holders 1414 and 1416 defines a funnel leading to a narrowing point or constriction, which then leads to the inside of the apparatus 1402. Both sets of elastomeric holders are extensions of an elastomeric hugger. The elastomeric hugger 1408 is supported by the support beams. The elastomeric hugger 1408 forms a pad within the inside perimeter of the support beams. The elastomeric hugger 1408 formed from elastomeric material provides a soft contact with the second medical device 1401 to which it is attached and, in addition, ensures a wide range of compatibility with medical devices due to the deformable and compliant material of construction. The elastomeric hugger 1408 can deform to fit medical devices of varying diameters. The apparatus 1402 further includes a ratcheting clip 1410, The ratcheting clip 1410 may be comprised of two pieces or, alternatively, the ratcheting clip 1410 can be a single piece with two opposing members with interlocking means. As best seen in FIG. 14D, the ratcheting clip 1410 includes a first interlocking arm 1411 and a second interlocking arm 1413. The interlocking arms 1411 and 1413 may be connected to one another similar to what is illustrated in FIG. 15 or, alternatively, each interlocking arm may be attached individually to the apparatus 1402. The interlocking arms 1411 and 1413 are flexible to wrap around a medical device being held within the elastic hugger 1408. To this end, the interlocking arms 1411 and 1413 can be made from a thin, flexible material at those sections where the interlocking arms wrap around the medical device. The ratcheting arms 1411 and 1413 wrap outside the elastomeric hugger 1408 and within the slots provided by each set of lateral and medial support beams and each set of lateral and medial elastomeric holders. Extending further out from the apparatus 1042 and beyond the thin, flexible sections, the interlocking arm 1411 extends outward, forming a comparatively rigid ear 1418. Generally perpendicular to the ear 1418, an extension 1420 with inside ratcheting teeth 1422 is provided. The extension 1420 generally defines an arcuate shape on the interior to match with a medical device. Opposite from the ratcheting arm 1411, a second ratcheting arm 1413 is provided. The ratcheting arm 1413 similarly includes a comparatively rigid ear 1415 extending from the thin section of ratcheting arm 1413. Generally perpendicular to ear 1415, an extension 1426 with outside ratcheting teeth 1428 is provided. As can be appreciated, the ratcheting teeth 1422 of extension 1420 and the ratcheting teeth 1428 of extension 1426 are made to interlock with one another, thereby providing a secure clamping action. The second extension 1426 is generally also provided as having an arcuate shape on the interior. Generally perpendicular to ear 1415, a second extension 1424 is provided on the ratcheting arm 1413. The second extension 1424 is a pressure foot. The pressure foot 1424 and the extension 1426 define a slot therebetween into which extension 1420 fits. The inside surface of the pressure foot 1424 applies a downward force on the extension 1420, which causes the ratcheting teeth 1422 to be more securely engaged with the ratcheting teeth 1428.

By placing a medical device 1401 within the interior of elastomeric hugger 1408, then wrapping both ratcheting arms 1411 and 1413 around the medical device 1401 such that the extension 1420 is inserted between the extensions 1426 and 1424 so as to engage inside ratcheting teeth 1422 with outside ratcheting teeth 1428 will provide a secure attachment between the medical device 1404 and the medical device 1401.

For example, in one representative embodiment, the first medical device to which the apparatus 1402 is attached can be an endoscope, and the second medical device 1401 can be a duodenal scope. This applies to all embodiments herein disclosed. The pressure foot 1424 keeps pressure on the interlocking ratcheting teeth 1422 and 1428 to prevent accidental disengagement. Once engaged to the medical device 1401, the ratcheting clip 1410 can be disengaged by applying a force against the inside of the ear 1415, which causes the pressure foot 1424 to lift, allowing the memory of the material to cause the extension 1420 to return to non-stressed condition and disengage the ratcheting teeth 1422 from the ratcheting teeth 1428. The ears 1418 and 1415 are used to apply pressure to bring the ratcheting arms 1411 and 1413 into engagement with one another and close around the medical device 1401. As pressure is applied on the ears 1418 and 1415, the elastomeric hugger 1408 may be deformed, thus securely holding the medical device 1401 to the medical device 1404.

Referring to FIG. 15, another embodiment of a ratcheting clip for attaching a first medical device to a second medical device is illustrated. The apparatus 1502 includes a central attachment point 1522 for securely attaching the apparatus 1502 to a first medical device (not shown). A similar attachment point may be provided for the embodiment illustrated in FIGS. 14A-14D, The attachment point 1522 is generally a solid, rigid structure that can withstand the forces being applied on the apparatus 1502. The apparatus is formed from two opposing ratcheting arms 1512 and 1514. The ratcheting arms 1512 and 1514 include sections closest to the connection point 1522 formed from a thin, flexible material. The ratcheting arms 1512 and 1514 are connected to one another at the connection point 1522, The ratcheting arms 1512 and 1514 further extend into ears 1504 and 1516, respectively, placed at the termination of the thin, flexible material sections. The ears 1504 and 1516 are generally positioned perpendicular to the length of the thin, flexible arms 1512 and 1514. The ears 1504 and 1516 may be generally rigid. The ratcheting arms 1512 and 1514 further comprise extension 1506 with inside ratcheting teeth 1508 and extension 1518 with outside ratcheting teeth 1520 such that when brought into engagement with one another, ratcheting teeth 1508 may interlock with ratcheting teeth 1520. In this embodiment, a pressure foot may not be necessary when the material is of a generally greater rigidity. The ratcheting arm 1512 further includes a pull tab 1510 connected to the end and outside surface of the extension 1506. Ratcheting arms 1512 and 1514 can wrap around a medical device 1501 by application of pressure on ears 1504 and 1516, Once engaged with each other, ratcheting teeth 1508 may be disengaged from ratcheting teeth 1520 by application of a pulling force on the pull tab 1510.

Referring to FIG. 16, an apparatus 1604 for attaching a first medical device 1602 to a second medical device 1601 is illustrated. The apparatus includes a base 1604 on a first medical device 1602 and a band or strap 1608 on a second medical device 1601. In this embodiment, the band or strap 1608 may be secured to the second medical device 1601 similar to the ratcheting clips disclosed above in connection with FIGS. 14 and 15. Alternatively, any means for securing a band or strap can be used, such as, but not limited to, adhesives, mechanical interlocking means, hook and loop fasteners (VELCRO®), adhesives, or mechanical fasteners. Furthermore, it is not necessary to have a band or strap. This embodiment relies on having flanged studs 1606 project outward from a location on the medical device 1601. A flanged stud may have a small diameter post extending from the support and the top of the post is fitted a flange of a larger perimeter than the post. One or any number of flanged studs 1606 may be provided on the exterior of the medical device 1601. The flanged studs are preferably, but not necessarily, in linear alignment with each other. The base 1604 on the medical device 1602 includes corresponding keyhole slots 1610 for each one of the flanged studs 1606 on the second medical device 1601, To attach medical device 1602 to medical device 1601, the base 1604 is pushed against the medical device 1601 such that the keyhole slots 1610 correspond to the flanged studs 1606 and are slid down to lock in place on the studs 1606. Further, a catch may be provided to further prevent the medical devices from accidentally disengaging. For removal, the slots 1610 are aligned with the flanges 1606, then the medical device 1602 is lifted up and pulled off from the flanged studs 1606.

One embodiment of the invention is of an apparatus for selectively securing a first medical device to a second medical device. The apparatus includes a clamp positioned on the first medical device including a first and second holding portion that open to receive the second medical device between the first and second holding portions and a locking mechanism that is selectively positioned to prevent the first and second holding portions from opening. The apparatus may have one of the first or second holding portions include a hook with a tab that is selectively positioned in a catch and the locking mechanism includes a pawl that secures the tab in the catch. The apparatus may have one of the holding portions being fixed to a clamp base and the other holding portion moving with respect to the clamp base and wherein the hook is secured to the holding portion that moves. The apparatus may have the pawl mounted on a rotating barrel. The apparatus may have the barrel being rotatable between a first position where the pawl does not prevent the tab from being removed from the catch and a second position where the pawl does prevent the tab from being removed from the catch. The first and second holding portions may be first and second jaws of a clamp, for example.

Another embodiment of the invention is of an apparatus for releasably securing a first medical device to a second medical device. The apparatus includes a pincer device including a first holding portion and a second holding portion that open and close around the second medical device by pivoting around a common pivot point. The apparatus includes a first handle and a second handle attached to the first holding portion and the second holding portion respectively and extending away from the common pivot point to open the pincer device by depressing the corresponding handles. The apparatus includes a spring that biases the first holding portion and the second holding portion towards a closed position. The apparatus may have a single spring that biases the first holding portion and the second holding portion. The apparatus may have a first spring that biases the first holding portion and a second spring that biases the second holding portion. The apparatus may have means for securing the pincer device to the first medical device. The apparatus may have the pincer being incorporated into a housing, and the means for securing the pincer device to the first medical device includes a pair of spring-biased tabs having serrations thereon that engage corresponding serrations in the housing. The apparatus may have spring biased tabs that can be disengaged from the serrations on the housing to allow the pincer to be removed from the first medical device. The first and the second holding portions may be first and second jaws.

Another embodiment of the invention is of an apparatus for releasably securing a first medical device to a second medical device. The apparatus includes a holding portion including a flexible strap secured thereto that has length that extends around the second medical device and a locking mechanism that secures an end of the strap in the holding portion. The apparatus may have the holding portion and the first medical device include first and second cooperating members that secure the holding portion to the first medical device. The apparatus may have the first and second members include a post and an aperture that receives the post. The apparatus may have the locking mechanism in the holding portion include a flexible tab having serrations that engage the serrations of the strap and a lever handle connected to the tab that disengages the serrations of the tab from the serrations on the strap. The holding portion may be a buckle, for example.

Another embodiment of the invention is of an apparatus for releasably securing a first medical device to a second medical device. The apparatus includes a first holding portion and a second holding portion connected to one another through a hinge that opens to allow the second medical device to fit between the holding portions, wherein the first holding portion includes a first extension that extends from the hinge and the second holding portion includes a second extension that extends from the hinge. The apparatus may have a locking mechanism that creates an over-center action that is connected between the first and the second extensions to secure the first and second extensions together and prevent the holding portions from opening. The apparatus may have the locking mechanism include a toggle joint having a first and a second leg rotatably coupled to the first and second extensions and joined to one another at a knee. The apparatus may have the knee being positionable so that the knee bends away from the hinge to allow the holding portions to open and the knee being positionable so that the knee bends toward the hinge to prevent the holding portions from opening. The apparatus may have the length of the hinge being less than the combined length of the first leg and the second leg. The apparatus may have one of the first or second legs include a lever that bends the knee towards or away from the hinge that joins the holding portions. The apparatus may be removably secured to the first medical device with a bracket. The apparatus may have the bracket include a pair of spaced arms that engage corresponding slots and an S-curve spring secured to a slot to disengage an arm from the slot. The first and second holding portions may be a first and a second jaw, for example.

Another embodiment is of an apparatus for attaching a first medical device to a second medical device. The apparatus includes a base supporting a clamp having a first and a second holding portion, each holding portion defining a curvature along the length of the holding portion, wherein the first and the second holding portions define an opening between the first holding portion and the second holding portion and the first holding portion has at least a first slot and the second holding portion has at least a second slot. The apparatus may have a sliding ring positioned within the first and the second slots so that the sliding ring is allowed to rotate in the holding portions to close the opening defined by the holding portions. The first and second holding portions may be a first and a second jaw, for example.

Another embodiment of the invention is of an apparatus for attaching a first medical device to a second medical device, wherein the apparatus is fastened to the first medical device and the apparatus is attachable and detachable to the second medical device. The apparatus includes a base supporting a clamp having a first holding portion and a second holding portion, wherein the first holding portion of the clamp is fixed in relation to the base and the other holding portion is moveable with respect to the base to allow the clamp to open. The apparatus may have a cam positioned between the base and the clamp, wherein the cam has an edge of varying thickness that is rotatable between the base and the second holding portion to engage the second holding portion and prevent the clamp from opening. The apparatus may have the cam on a disk that is rotatably secured to the base. The apparatus may have the disk include a handle that is moved by a user to rotate the cam. The first and second holding portions may be a first and a second jaw, for example.

Another embodiment of the invention is of an apparatus for attaching a first medical device to a second medical device. The apparatus includes a strap connected to the first medical device having a length that extends around the second medical device. The apparatus includes a slot on the first medical device for receiving an end of the strap. The apparatus includes a cam in the slot that allows the strap to be advanced into the slot and resists the strap from being withdrawn from the slot. The apparatus may have the cam that upon pivoting on an axis creates a wide passage that allows insertion of the strap through the slot, and the cam upon pivoting on an axis creates a narrow passage that prevents the strap from being withdrawn from the slot. The apparatus may have the cam having an eccentric lobe that creates the narrow passage through the slot. The apparatus may have the cam having an off center axis. The apparatus may have the cam having a textured surface to engage the surface of the strap.

Another embodiment of the invention is of an apparatus for attaching a first medical device to a second medical device. The apparatus includes a strap connected to the first medical device having a length that extends around the second medical device, wherein at or near the end of the strap, the strap has either the hook or the loop portion of a hook and loop fastener. The apparatus includes a corresponding hook or loop portion of the hook and loop fastener being placed on the first medical device to secure the strap when placed around the second medical device.

Another embodiment of the invention is of an apparatus for attaching a first medical device to a second medical device. The apparatus includes a strap connected to the first medical device and having a length that extends around the second medical device and including a number of serrations. The apparatus includes a ratcheting mechanism that receives an end of the strap, the ratcheting mechanism having a lever with serrations that engage the serrations on the strap and a pawl to prevent the strap from releasing after ratcheting.

Another embodiment of the invention is of an apparatus for attaching a first medical device to a second medical device. The apparatus includes a base having a first and a second hinge. The apparatus includes a first holding portion connected to the first hinge and a second holding portion connected to the second hinge, wherein the first holding portion and the second holding portion open to receive the second medical device, wherein each holding portion includes a boss that engages as the holding portions are closed and applies pressure to the holding portions to keep them in a closed position. The first and the second holding portions create an over-center action that secures the medical device in the apparatus. The first and second holding portions may be a first and a second jaw, for example.

Another embodiment of the invention is of an apparatus for attaching a first medical device to a second medical device. The apparatus includes a base having a clamp including a first holding portion and a second holding portion each holding portion defining a curvature along the length of the holding portion, wherein the holding portions are semi-rigid and permit some flexing when placed under pressure, wherein the holding portions further define an upper radius of curvature along the upper edge and a lower radius of curvature along the lower edge so that the upper radius of curvature is greater than the lower radius of curvature. The apparatus may have the first and the second holding portions together define a funnel shape. The first and the second holding portions may be a first and a second jaw, for example.

Another embodiment of the invention is of an apparatus for attaching a first medical device to a second medical device. The apparatus includes a base attachable to the first medical device. The apparatus includes a first hook positioned on the base at a first elevation near the top of the base. The apparatus includes a second hook positioned on the base at a second elevation below the first hook so that the hooks are both facing in from opposite directions, the hooks being arranged to engage opposite sides of the second medical device. The apparatus includes a sliding latch on the base that is aligned in the same direction as the first hook that slides to secure a second medical device that is placed in contact with the first and second hooks.

Another embodiment of the invention is of an apparatus for attaching a first medical device to a second medical device. The apparatus includes a first and a second ratcheting arm, which are both attachable to a first medical device. Each ratcheting arm may be formed from a thin, flexible, and elongated strip of material that flexes to wrap around a second medical device. The ratcheting arms may be connected to one another at the center or may be independently attached to the first medical device. The ratcheting arms each include an extension with ratcheting teeth formed on a surface thereof. One ratcheting arm comprises ratcheting teeth on the lower surface, where the opposite ratcheting arm comprises ratcheting teeth on the upper surface. Each ratcheting arm may further include an ear which is a projection extending generally perpendicular to the thin, flexible material. The ears are used for opening and closing the ratcheting arms around a second medical device. One ratcheting arm further includes a pressure foot. The pressure foot is placed alongside the ratcheting teeth on one ratcheting arm so the ratcheting teeth of the second ratcheting arm are engaged between the ratcheting teeth and the pressure foot of the first ratcheting arm.

Another embodiment of the invention is of an apparatus, such as a ratcheting clip, for attaching a first medical device to a second medical device. The apparatus includes a first and a second ratcheting arm, which are both attachable to a first medical device. Each ratcheting arm may be formed from a thin, flexible, and elongated strip of material that flexes to wrap around a second medical device. The ratcheting arms may be connected to one another at the center or may be independently attached to the first medical device. The ratcheting arms each include an extension with ratcheting teeth formed on a surface thereof. One ratcheting arm comprises ratcheting teeth on an inside surface, where the opposite ratcheting arm comprises ratcheting teeth on the outside surface. Each ratcheting arm may further include an ear which is a projection extending generally perpendicular to the thin, flexible material. The ears are used for opening and closing the ratcheting arms around a second medical device. One ratcheting arm further includes a pressure foot. The pressure foot is placed alongside the ratcheting teeth on one ratcheting arm so the ratcheting teeth of the second ratcheting arm are engaged between the ratcheting teeth and the pressure foot of the first ratcheting arm. Embodiments that do not have a pressure foot can include a pull tab that can be used to disengage one ratcheting arm from the other ratcheting arm. Embodiments of ratcheting clips can further have a deformable or elastomeric hugger within the inside perimeter of the ratcheting arms.

Another embodiment of the invention is of an apparatus for attaching a first medical device to a second medical device. The first medical device can include a base with one or more keyhole slots. The second medical device can include one or more flanged studs for each of the keyhole slots on the first medical device. The flanged studs may be attached to a band or strap which wraps around the circumference of a second medical device.

In all of the embodiments disclosed above, the apparatuses are attachable to devices including medical devices such as, but not limited to, endoscopes, duodenal scopes, as well as any other medical device, and including devices having illumination or imaging means.

While illustrative embodiments have been illustrated and described, it will be appreciated that various changes can be made therein without departing from the spirit and scope of the invention.

The embodiments of the invention in which an exlusive property or privilege is claimed are defined as follows:

1. An apparatus for attaching a first medical device to a second medical device, the apparatus comprising:
   a first portion configured for attachment to the first medical device, wherein the first portion is slidable relative to the first medical device for coupling the apparatus to the first medical device; and
   a second portion for coupling to, and uncoupling from, the second medical device, wherein the second portion is configured to at least partially surround a perimeter of the second medical device.

2. The apparatus of claim 1, wherein the second portion includes at least one of a strap, a ring, or a clamp configured to at least partially surround a perimeter of the second medical device.

3. The apparatus of claim 2, wherein the second portion includes the clamp, and wherein the clamp includes a first jaw and a second jaw.

4. The apparatus of claim 3, wherein each of a first end of the first jaw and a second end of the second jaw includes a radially outward flare configured to guide the second medical device into engagement with the second portion.

5. The apparatus of claim 3, wherein the first jaw and second jaw are biased towards one another.

6. The apparatus of claim 3, wherein the clamp is coupled to a body of the apparatus, wherein the first jaw is fixedly coupled to the body, and wherein the second jaw is movably coupled to the body.

7. The apparatus of claim 1, wherein the second portion is configured to at least partially surround a perimeter of a shaft of the second medical device.

8. The apparatus of claim 1, wherein the first medical device is an endoscope, and the second medical device is a duodenal scope.

9. The apparatus of claim 1, wherein the second portion further comprises a locking mechanism including a lever.

10. The apparatus of claim 1, wherein the second portion comprises a deformable material.

11. The apparatus of claim 1, wherein the apparatus is configured to slide relative to the first medical device from below the first medical device.

12. An apparatus for attaching a first medical device to a second medical device, the apparatus comprising:
    a first component configured for attachment to the first medical device; and
    a second component for coupling to, and uncoupling from, the first component,
    wherein, to couple the second component to the first component, the second component slides relative to the first component, and wherein the second component is configured to couple to, and uncouple from, the second medical device.

13. The apparatus of claim 12, wherein the first component is configured for attachment to the first medical device via a mechanical fastener or an adhesive.

14. The apparatus of claim 12, wherein the second component includes at least one of a strap, a ring, or a clamp configured to at least partially surround a perimeter of the second medical device.

15. The apparatus of claim 14, wherein at least one of the strap, the ring, or the clamp is configured to at least partially surround a perimeter of a shaft of the second medical device.

16. The apparatus of claim 12, wherein the first component is configured for detachment from the first medical device.

17. The apparatus of claim 12, wherein the first medical device is an endoscope and the second medical device is a duodenal scope.

18. An apparatus for attaching a first medical device to a second medical device, the apparatus comprising:
    a first portion configured for attachment to the first medical device, wherein the first portion is slidable relative to the first medical device for coupling the apparatus to the first medical device; and
    a second portion including at least one of a strap, a ring, or a clamp for coupling to, and uncoupling from, the second medical device.

19. The apparatus of claim 18, wherein the second portion includes the clamp, and wherein the clamp includes a first jaw and a second jaw, wherein the clamp is coupled to a body of the apparatus, wherein the first jaw is fixedly coupled to the body, and wherein the second jaw is movably coupled to the body.

20. The apparatus of claim 19, wherein the at least one of the strap, the ring, or the clamp is configured to at least partially surround a perimeter of the second medical device, and wherein the second portion includes a locking mechanism for locking the strap, the ring, or the clamp in position around the second medical device.

21. The apparatus of claim 18, wherein the first medical device is an endoscope and the second medical device is a duodenal scope.

* * * * *